United States Patent
Yoshii et al.

(10) Patent No.: US 7,283,912 B2
(45) Date of Patent: Oct. 16, 2007

(54) DNA PROBE DESIGN DEVICE AND INFORMATION PROCESSING METHOD FOR DNA PROBE DESIGN

(75) Inventors: Hiroto Yoshii, Tokyo (JP); Toshifumi Fukui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 494 days.

(21) Appl. No.: 10/805,292

(22) Filed: Mar. 22, 2004

(65) Prior Publication Data

US 2005/0026176 A1 Feb. 3, 2005

(30) Foreign Application Priority Data

Apr. 2, 2003 (JP) ............................. 2003-099464
Mar. 8, 2004 (JP) ............................. 2004-064494

(51) Int. Cl.
G06F 19/00 (2006.01)
G06F 15/00 (2006.01)
G11C 17/00 (2006.01)

(52) U.S. Cl. .............................. 702/20; 700/1; 365/94
(58) Field of Classification Search ..................... None
See application file for complete search history.

(56) References Cited

U.S. PATENT DOCUMENTS 2,878,040 A    3/1959   Hobbs
6,476,215 B1  11/2002   Okamoto et al. .......... 536/25.3
2002/0146715 A1  10/2002  Okamoto et al. ............... 435/6
2002/0147330 A1  10/2002  Yamamoto et al. ....... 536/24.32
2002/0183933 A1  12/2002  Webster et al. ............... 702/19

FOREIGN PATENT DOCUMENTS

JP    10-272000    10/1998
JP    11-187900     7/1999

OTHER PUBLICATIONS

Rouillard et al. OligArray: genome-scale oligonucleotide design for microarrays. Bioinformatics vol. 18, pp. 486-487 (2002).*
Michael Zuker, "Calculating Nucleic Acid and Secondary Structure", Structural Biology, 10, 303-310, 2000.

* cited by examiner

Primary Examiner—John S Brusca
(74) Attorney, Agent, or Firm—Fitzpatrick, Cella, Harper & Scinto

(57) ABSTRACT

The number of times of manifestation of each of a plurality of partial base sequences obtained from own base sequence data containing a target base sequence is counted, and held as an own frequency table. The number of times of manifestation of each of the plurality of partial base sequences is also counted for competing base sequence data to be distinguished from the own base sequence data, and held as a competing frequency table. In a probe evaluation step, the frequency information in the own and competing frequency tables is displayed so as to be comparable with reference to the partial base sequences, and at least one of the plurality of partial base sequences is determined according to instruction operations made by a user, thereby forming probe candidates based on the determined partial base sequences.

16 Claims, 17 Drawing Sheets

| BASE SEQUENCE | FREQUENCY (UNIQUENESS) |
|---|---|
| AAAAAAAAA | 1000 |
| AAAAAAAAT | 10 |
| ... | ... |
| ... | ... |
| GTAGATCCA | 3 |
| GTAGATCCT | 5 |
| ... | ... |
| ... | ... |
| CCCCCCCCC | 0 |

FIG. 15

DNA PROBE DESIGN DEVICE AND INFORMATION PROCESSING METHOD FOR DNA PROBE DESIGN

BACKGROUND OF THE INVENTION

1. Field of the Invention

The present invention relates to the art of designing oligonucleotide probes suitable for a nucleic acid sequence analysis system using so-called DNA microarrays or the like.

2. Description of the Related Art

There conventionally have been known systems for gene manifestation and sequence determining systems using DNA microarrays, as described in Japanese Patent Laid-Open No. 10-272000 and Japanese Patent Laid-Open No. 11-1187900. With the system disclosed in these Patent Documents, there is the need to design probes for hybridizing with specimens beforehand, unlike DNA microarrays created through spots with cDNA. In the event that a suitable probe can be designed well, information regarding base sequence fragments in a specimen can be obtained at an extremely high probability.

With this system, it is unusual for even the longest base sequences used as probes to reach 100 or more in length, and short base sequences are just a few bases in length. That is to say, with the system disclosed in these Patent Documents, a particular base sequence is trapped using a probe of a base sequence which is far shorter than cDNA. Accordingly, there is the need for the uniqueness of a portion of the base sequence used as the probe in the DNA to be extremely high.

With the conventional selection method for selecting a portion with a high level of uniqueness described above, uniqueness evaluation is performed with regard to general sequences. For example, in the event of creating a DNA microarray for DNA from a human genome, uniqueness was checked for all human genome base sequences, and a portion with a high level of uniqueness was selected as a probe base sequence.

However, there has been a problem with the conventional selecting method in that, in the event that extremely similar base sequences are contained in a specimen, and the similar base sequences include base sequences belonging to one group and base sequences belonging to another group, determining whether each base sequence belongs to that group is extremely difficult. More specifically, at the time of making a determination for an infection or the like, there has been the problem that it is extremely difficult to find a probe which exhibits the same degree of hybrid strength regarding a DNA base sequence of the same strain of bacteria and which exhibits a different degree of hybrid strength regarding a DNA base sequence of another strain of bacteria.

Also, with the conventional method, in the event of searching for locations unique to an organism or common locations in polymorphic loci in extremely similar base sequences, all of the polymorphic base sequences are displayed for the subject organism using multiple alignment or the like, and human workers view these and select appropriate portions. This conventional method allows human error, and also results in difference in results from one worker to another.

SUMMARY OF THE INVENTION

The present invention has been made in light of the above-described problems, and accordingly, it is an object of the present invention to provide for probe design which is accurate and has high reproducibility.

To this end, according to a first aspect of the present invention, an information processing method for designing a DNA probe comprises: a first counting step for counting, with regard to a first base sequence data group containing a target base sequence, the number of times of manifestation of each of a plurality of partial base sequences obtained from data of the target base sequence, and holding frequency information obtained by the counting; a second counting step for counting, with regard to a second base sequence data group to be distinguished from the first base sequence data group, the number of times of manifestation of each of the plurality of partial base sequences, and holding frequency information obtained by the counting; and a formation step for forming probe candidates based on frequency information held in the first and second counting steps.

The formation step for forming probe candidates based on frequency information held in the first and second counting steps-may further comprise: a display step for displaying frequency information held in the first and second counting steps, so as to be comparable with reference to the plurality of partial base sequences; and a formation step for determining at least one of the plurality of partial base sequences according to instruction operations made by a user, and forming probe candidates based on the determined partial base sequences.

The method may further comprise a third counting step for counting, with regard to the first base sequence data group and the second base sequence data group, the position and length of partial base sequences common to both, and holding information obtained thereby.

Probe creating may be performed with regard to regions between common base sequences obtained in the third counting step, or with regard to all regions between common base sequences obtained in the third counting step.

The formation step for forming probe candidates based on frequency information held in the first and second counting steps may comprise: a searching step for searching for partial base sequences wherein the frequency obtained in the first counting step exceeds a first predetermined value, and wherein the frequency obtained in the second counting step is smaller than a second predetermined value; and a formation step for forming probe candidates based on the partial base sequences searched in the searching step.

The searching step may be a searching step for searching for partial base sequences wherein the frequency obtained in the first counting step exceeds a first predetermined value, and wherein the frequency obtained in the second counting step is smaller than a second predetermined value, with regard to regions between common regions obtained in the third counting step.

The plurality of partial base sequences may be obtained by acquiring a base sequence by extracting a predetermined number of bases from the target base sequence data, while shifting the head position thereof.

The first base sequence data group may be base sequence data including a plurality of polymorphs of a target organism species, and the second base sequence data group base sequence data including a plurality of polymorphs of a organism species other than the target organism species.

The method may further comprise a first selecting step for selecting probe candidates to be used for a probe set with regard to probe candidates formed in the forming step, by adding and deleting bases at the head and end such that the melting temperature is around the same as that of other probes making up the probe set, or for calculating the probe melting temperature for the probe candidates formed in the forming step, and selecting probe candidates to be used for a probe set based on the calculated melting temperature.

The method may further comprise a second selecting step for calculating the probability of formation of secondary structures with regard to the probe candidates formed in the forming step, and selecting probe candidates to be used for a probe set based on the calculation results, and may further comprise a third selecting step for calculating a degree of matching with regard to the probe candidates formed in the forming step, and selecting probe candidates to be used for a probe set based on the degree of matching.

According to a second aspect of the present invention, a DNA probe design device comprises: first counting means for counting, with regard to a first base sequence data group containing a target base sequence, the number of times of manifestation of each of a plurality of partial base sequences obtained from data of the target base sequence, and holding frequency information obtained by the counting; second counting means for counting, with regard to a second base sequence data group to be distinguished from the first base sequence data group, the number of times of manifestation of each of the plurality of partial base sequences, and holding frequency information obtained by the counting; display means for displaying frequency information held by the first and second counting means, so as to be comparable with reference to the plurality of partial base sequences; and formation means for determining at least one of the plurality of partial base sequences according to instruction operations made by a user, and forming probe candidates based on the determined partial base sequences.

The DNA probe design device may further comprise third counting means for counting, with regard to the first base sequence data group and the second base sequence data group, the position and length of partial base sequences common to both, and holding information obtained thereby.

The display means may add common information held by the third counting means to the frequency information held by the first and second counting means, and display the information so as to be comparable with reference to the plurality of partial base sequences, and probe creating may be performed with regard to regions between common base sequences obtained in the third counting means.

According to a third aspect of the present invention, a DNA probe design device comprises: first counting means for counting, with regard to a first base sequence data group containing a target base sequence, the number of times of manifestation of each of a plurality of partial base sequences obtained from data of the target base sequence, and holding frequency information obtained by the counting; second counting means for counting, with regard to a second base sequence data group to be distinguished from the first base sequence data group, the number of times of manifestation of each of the plurality of partial base sequences, and holding frequency information obtained by the counting; searching means for searching for partial base sequences wherein the frequency obtained by the first counting means exceeds a first predetermined value, and wherein the frequency obtained by the second counting means is smaller than a second predetermined value; and formation means for forming probe candidates based on the partial base sequences searched by the searching means.

According to a fourth aspect of the present invention, a DNA probe design device comprises: first counting means for counting, with regard to a first base sequence data group containing a target base sequence, the number of times of manifestation of each of a plurality of partial base sequences obtained from data of the target base sequence, and holding frequency information obtained by the counting; second counting means for counting, with regard to a second base sequence data group to be distinguished from the first base sequence data group, the number of times of manifestation of each of the plurality of partial base sequences, and holding frequency information obtained by the counting; third counting means for counting, with regard to the first base sequence data group and the second base sequence data group, the position and length of partial base sequences common to both, and holding information obtained thereby; searching means for searching for, with regard to regions between common base sequences obtained by the third counting means, partial base sequences wherein the frequency obtained by the first counting means exceeds a first predetermined value, and wherein the frequency obtained by the second counting means is smaller than a second predetermined value; and formation means for forming probe candidates based on the partial base sequences searched by the searching means.

Further aspects of the present invention are a control program for causing a computer to execute the above information processing method, a storage medium storing the control program, a DNA microarray having nucleic acid probes designed by the probe design method, and a nucleic acid testing method using the DNA microarray.

Thus, oligonucleotide probe design optimal for a DNA microarray system can be realized, whereby accurate and reproducible probe design can be realized. This is advantageous in that more accurate species and individual identification information can be obtained.

Further objects, features and advantages of the present invention will become apparent from the following description of the preferred embodiments (with reference to the attached drawings).

BRIEF DESCRIPTION OF THE DRAWINGS

FIG. 15 is a diagram illustrating a user interface according to the second embodiment, showing SEQ ID NO:171.

DESCRIPTION OF THE PREFERRED EMBODIMENTS

Next, preferred embodiments of the present invention will be described, with reference to the attached drawings.

First Embodiment

[Description of Probe Design Method]

Figure 2:
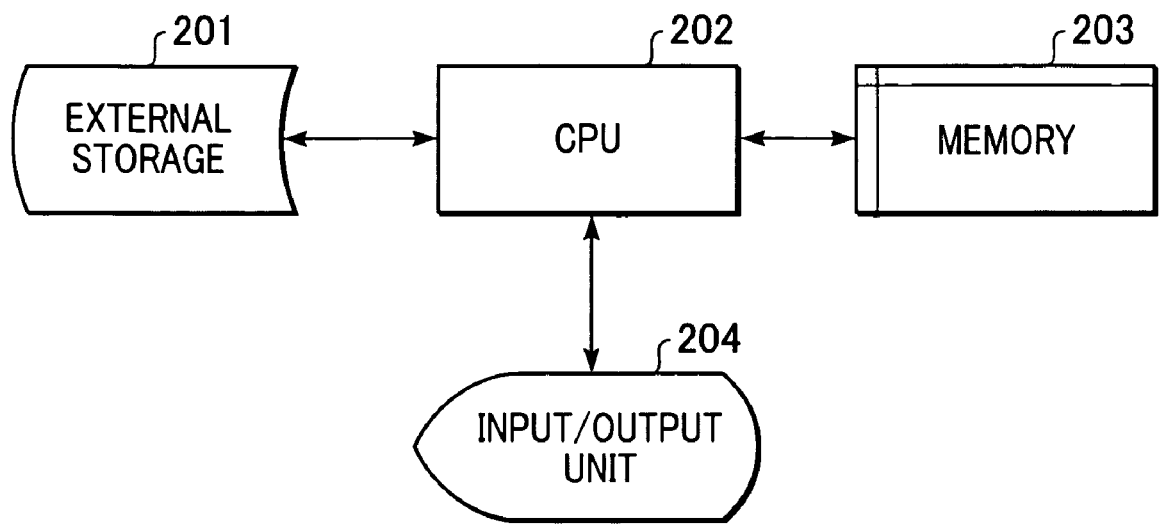
FIG. 2 is a block diagram illustrating the configuration of an information processing device to which the probe design method according to the first embodiment is applicable.

FIG. 2 is a block diagram illustrating the configuration of an information processing device to which the probe design method according to a first embodiment of the present embodiment is applied. The probe design method according to the present embodiment is installed in a device comprising an external storage device 201, central processing unit (CPU) 202, memory 203, and input/output unit 204. That is to say, probe design method according to the present embodiment can be installed in a personal computer, workstation, or the like.

In FIG. 2, the external storage device 201 stores programs for realizing the probe design method according to the present embodiment, various types of base sequence data and parameters (DNA (oligonucleotide) probe length, melting temperature, etc.), and also functions to hold the probe array itself selected by the present embodiment. The CPU 202 performs actions such as executing probe design programs, controlling all devices, and so forth. The memory 203 temporarily stores programs, subroutines, and data to be used by the CPU 202. The input/output unit 204 includes a display, keyboard, pointing device, and so forth, for interacting with the user. In may cases, the trigger for executing programs for realizing the probe design method according to the present invention is output by the user via the input/output unit. Also, the user views results and controls program parameters via this input/output unit.

Figure 1:
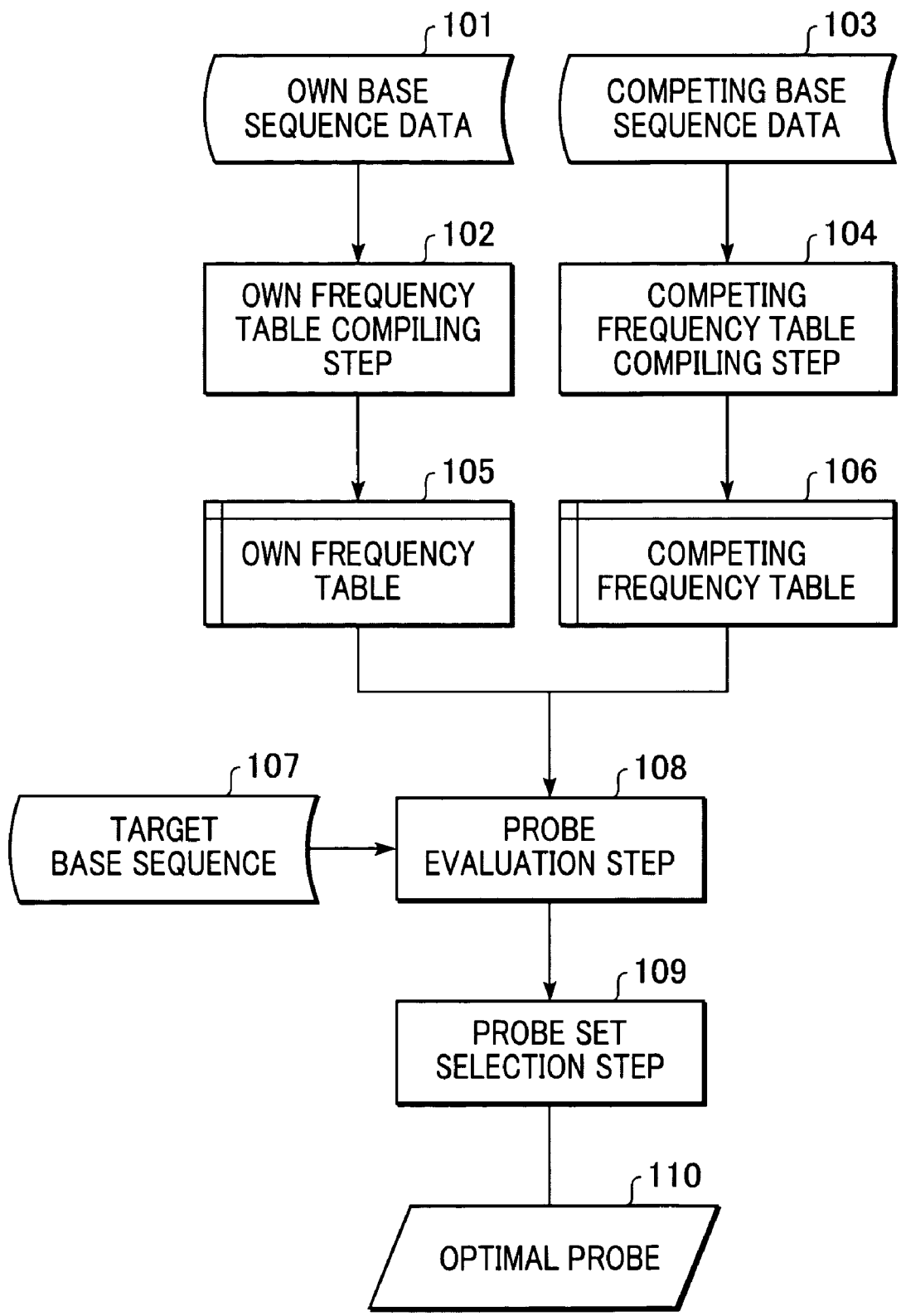
FIG. 1 is a diagram illustrating the overview of a probe design method according to a first embodiment of the present invention

FIG. 1 is a flowchart describing the processing procedures for the probe design method according to the present embodiment. Here, reference numeral 101 denotes own base sequence data, and in the event that the target base sequence 107 is a base sequence of a particular strain of a particular bacterium for example, and comprises data of base sequences of various strains of the same bacterium as the target base sequence 107. Reference numeral 102 denotes an own frequency table creating step, which is a step for counting the frequency of partial sequences contained in the own base sequence data 101, and creating an own frequency table 105. Reference numeral 103 denotes competing base sequence data competing with the target base sequence, and comprises base sequence data of various strains of bacteria different from the bacterium for the own base sequence data 101. Reference numeral 104 denotes a competing frequency table creating step, which is a step for counting the frequency of partial base sequences contained in the competing base sequence data 103, and compiling a competing frequency table 106.

Reference numeral 108 denotes a probe evaluation step, which is a step for yielding probe candidates from the target base sequence 107 using the own frequency table 105 and competing frequency table 106. Reference numeral 109 denotes a probe set selecting step, where a suitable probe set is selected from the probe candidates obtained as a result of the probe evaluation step 108. Reference numeral 113 denotes the optimal probe ultimately obtained. While the method for sorting the probe candidates in the probe set selecting step 110 will be described later, storing is carried out using, for example, (1) base sequence length, (2) melting temperature, (3) probability of generating secondary structures, and (4) similarity of base sequence. Reference numeral 110 denotes the ultimately obtained optimal probe. Note that in the probe design processing shown in FIG. 1, input is the target base sequence 107, and output is the optimal probe 110.

Figure 3:
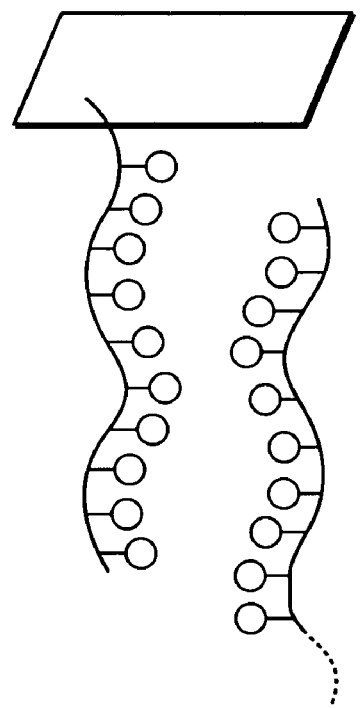
FIG. 3 is a diagram describing a hybridization reaction.

Prior to describing the data and processing shown in FIG. 1, a description will be made to provide the reader with background knowledge regarding the present invention. FIG. 3 is a diagram illustrating the way that hybridization is carried out on a DNA microarray. In almost all cases in organisms, a DNA base sequence has a double-helix structure, with the two chains being joined by hydrogen bonding between the bases. On the other hand, the base sequence for RNA often exists as a single strand. The types of bases are the four of ACGT for DNA, and the four of ACGU for RNA, and in either case, the pairs of bases which can be hydrogen bonded are A-T (U) and C-G. Hybridization refers to a state wherein single strands of nucleic acid molecules are bonded through a base sequence at one portion. The reaction assumed with the present invention is one wherein the nucleic acid molecule (probe) toward the top which is connected to the substrate shown in FIG. 3 is shorter than the nucleic acid molecule in the specimen, shown toward the bottom. Accordingly, in the event that the nucleic acid molecule in the specimen contains the probe base sequence, the hybridization reaction succeeds, and the target nucleic acid molecule in the specimen is trapped.

Figure 4:
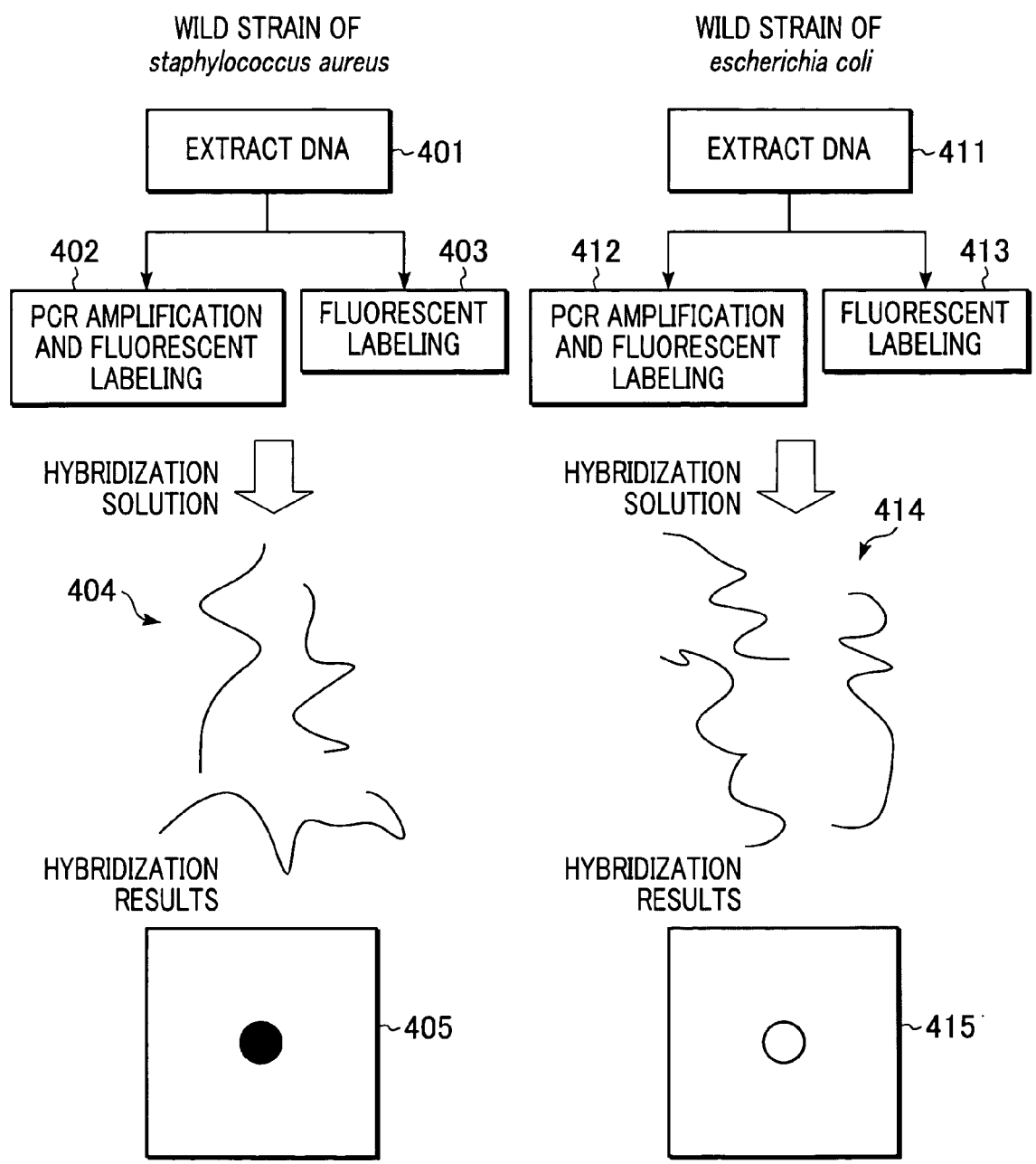
FIG. 4 is a diagram describing experiment procedures for determining an infection by DNA microarray.

Next, the principle of DNA microarray for determining a bacterium for an infection will be described with reference to FIG. 4. Let us say that the DNA microarray shown in FIG. 4 has been created to determine, for example, *staphylococcus aureus*. Shown to the left in FIG. 4 is a processing system from a wild strain of *staphylococcus aureus,* and to the right is a processing system from a wild strain of *escherichia coli*. The left can be thought of as a flow for processing the blood of a patient infected by *staphylococcus aureus,* and the right as a flow for processing the blood of a patient infected by *escherichia coli.*

Both basically perform the same processing. That is to say, first, DNA is extracted from the blood, phlegm, etc., of the patient with a bacterial infection, for example (401, 411). At this time, there is the possibility that this may contain human DNA originating from body cells of the patient. In the event that the amount of extracted DNA is small, the sample is amplified by PCR or a like method. Generally, a fluorescent substance or a substance which can be bonded with a fluorescent substance is included as an indicator (402, 412).

In the event that this amplification is not performed, the extracted DNA is used, and a fluorescent substance or a substance which can be bonded with a fluorescent substance is mixed in as an indicator while creating a complementary strand, or, a fluorescent substance or a substance which can be bonded with a fluorescent substance is directly added to the extracted DNA as an indicator (403, 413).

Normally, PCR amplification is performed so as to amplify the portion of a base sequence making up a ribosome RNA called 16s (16s rRNA) in the event that determining an infectious bacteria is the object. In this case, the PCR primer for the *staphylococcus aureus* shown to the left in FIG. 4, and the PCR primer for the *escherichia coli* to the right side, are almost the same. More specifically, multiplex PCR using a primer set capable of amplifying the locus coding 16s rRNA of any bacterium is preferable. In this case, both the left and right hybridization solutions (404, 414) in FIG. 4 consequently contain multiple types of base sequences. The reason for this will be described in detail with reference to the subsequent drawing.

On the other hand, in the event that a more detailed base sequence analysis is preferred, a PCR primer set for *staphylococcus aureus*, and a PCR primer set for *escherichia coli*, for example, are set separately. In this case, setting the primer so as to selectively amplify only a particular portion of the bacterium genome will result in the types of base sequences contained in the hybridization solution being very restricted. However, even in this case, there are several bacterium strains which exist in the natural world, so cases wherein there is only one type of base sequence in the hybridization solution are rare.

Now, in the event that the DNA microarray designed for determining the *staphylococcus aureus* works correctly, the spot will react positively in the hybridization solution 404 (405) and react negatively in the hybridization solution 414 to the right (415). In the same way, in the event that the DNA microarray designed for determining the *escherichia coil* works correctly, the spot will react negatively in the hybridization solution 404, and react positively in the hybridization solution 414. Of course, the bacterium may be determined using a DNA microarray wherein several types of spots, each reacting uniquely to different bacteria, are arrayed.

Next, the reason why multiple types of base sequences exist in the hybridization solution in FIG. 4 will be described with reference to FIG. 5. Bacteria in the natural world tend to frequently mutate. As a result, there may be multiple types of major strains, which have survived natural selection, coexisting simultaneously. For example, bacteria strains that cause a so-called "hospital infection" emerge from a bacterium, which normally has no drug resistance, mutating and consequently acquiring drug resistance. Once such drug resistance is acquired, the bacterium may manifest itself having robust reproductive ability even in sanitary environments, which are aggressively sterilized. Thus, it is proper to assume that there are several variations to each base sequence of any bacterium that exists in the natural world.

Figures 5, 6:
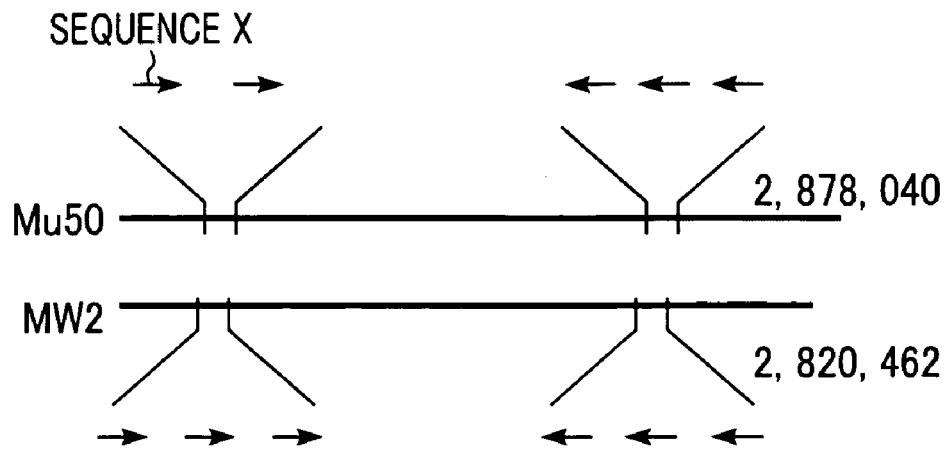
FIG. 5 is a diagram illustrating the genome structure of another strain of staphylococcus aureus.
FIG. 6 is a diagram illustrating an example of a frequency table according to the embodiment.

FIG. 5 illustrates the genome structure of two strains of *staphylococcus aureus*, Mu50 and MW2. The total number of bases for the genome of each strain is 2,878,040, and 2,820, 462, respectively, and are not the same. Note that in FIG. 5, the left-to-right direction is the direction from the 5' end toward the 3' end, with the base sequences shown in order following this direction. Further, while the loci coding the 16s ribosome RNA (16s rRNA) for Mu50 is 2 in the forward direction and 3 in the reverse direction for a total of 5, for MW2 this is 3 in the forward direction and 3 in the reverse direction for a total of 6. The base sequences for each locus of the 16s rRNA are very similar, but not identical. That is to say, even in the event that there is just one strain of the bacterium in the body of an infected patient being diagnosed, preparing the hybrid solution with a standard process such as shown in FIG. 4 results in multiple types of base sequences existing in the hybridization solution. Designing a probe exhibiting the same sort of hybrid strength with regard to these multiple base sequences is the object of the probe design method according to the present embodiment.

In order to achieve this object, with the probe design method according to the present embodiment, frequency tables are compiled separately for a set of base sequences that belong to the same group as the target base sequence (own base sequence data 101) and a set of base sequences that belong to a group competing with the former group (competing base sequence data 103) as shown in FIG. 1. In the example shown in FIG. 4, a collection of base sequences of 16s rRNA at various loci from various strains of *staphylococcus aureus* make up the own base sequence data 101, and a collection of base sequences of 16s rRNA at various loci from various strains of bacteria other than *staphylococcus aureus*, such as *escherichia coil* and *haemophilus influenzae*, make up the competing base sequence data 103.

The way in which a frequency table is compiled from such a base sequence is shown in FIG. 6. To compile a frequency table, the number of times a partial sequence of a length "n" (in FIG. 6, n=9) is present in the base sequence data is counted. The variations of base an n-long base sequence is 4 to the n'th power, so in FIG. 6, the number of lines is $4^n$. Note that in FIG. 6, the lower the frequency of emergence, the higher the uniqueness of the partial sequence, so the frequency multiplied by minus 1, for example, represents the uniqueness.

That is to say, in the own frequency table creating step 102, reference is made to the own base sequence data 101 storing the base sequences for 16s rRNA of various strains of the bacterium to be detected, the number of occurrences is counted for all partial base sequences having a length of n, and the results are compiled in a table as shown in FIG. 6, thereby creating the own frequency table 105. In the same way, in the competing frequency table creating step 104, reference is made to the competing base sequence data 103 storing the base sequences for 16s rRNA of various strains of bacteria other than the bacterium to be detected (i.e., a bacterium to be distinguished from the bacterium to be detected), the number of occurrences is counted for all partial base sequences having a length of n, and the results are compiled in a table as shown in FIG. 6, thereby creating the competing frequency table 106.

Figure 7:
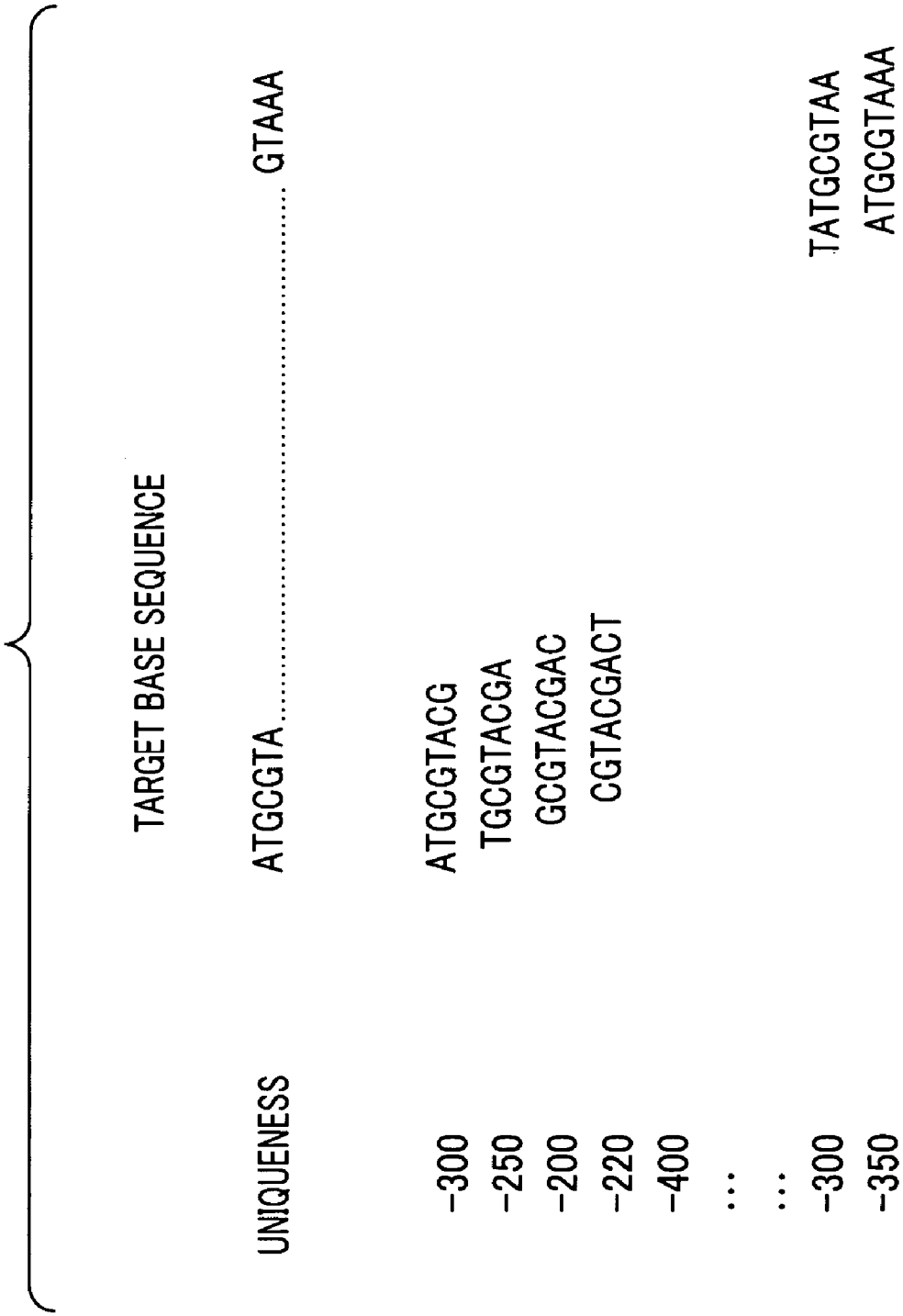
FIG. 7 is a diagram illustrating an example of scanning the uniqueness of a target base sequence.

Next, the frequency or uniqueness of the partial sequences (base sequences of n bases) according to the target base sequence 107 shown in FIG. 1 is obtained using the frequency table. This is shown in FIG. 7, wherein the target base sequence 107 is, for example, the leftmost 16s rRNA coding locus (sequence X) of the *staphylococcus aureus* of strain Mu50 in FIG. 5, and so forth. In the probe evaluation step 108, reference is made to the own frequency table 105 and the competing frequency table 106 to obtain the frequency (uniqueness) of the sequentially obtained partial sequences from the target base sequence 107, which are evaluated. This is shown in a graph in FIG. 8.

Figure 8:
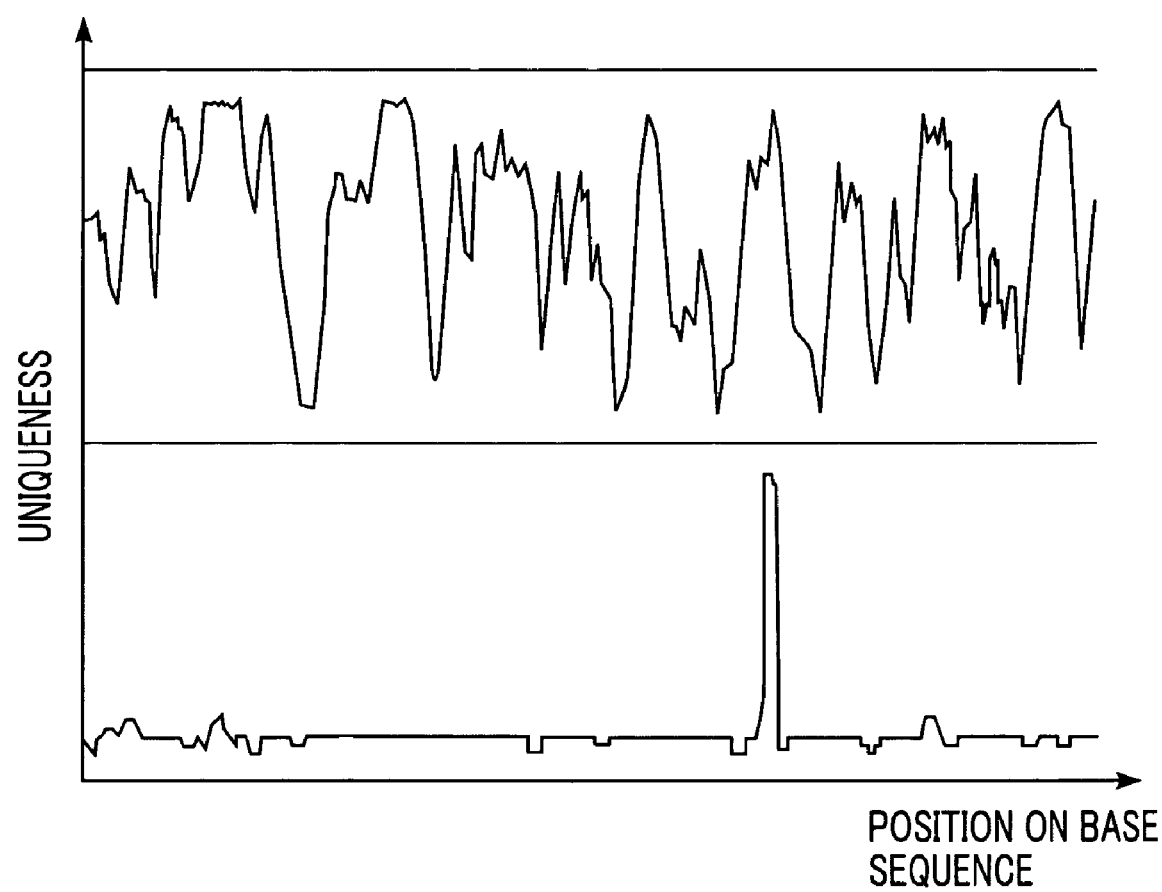
FIG. 8 is a graph plotted from values from a competition frequency table and probe design table.

In FIG. 8, the horizontal axis is the position of the partial sequence on the target base sequence, and in the event that the 16s rRNA portion is to be checked for example, the length is around 1500. The vertical axis is the uniqueness of the partial base sequence at that portion, and is obtained by multiplying the value in the frequency table by minus 1, for example. In FIG. 8, the graph at the top represents the uniqueness obtained based on the competing frequency table 106 in FIG. 1, and the graph at the bottom represents the uniqueness obtained based on the own frequency table 105 in FIG. 1.

For example, in the case of the graph shown in FIG. 8, a portion with a high level of uniqueness of the target base sequence exists at a portion around ⅔ from the head of the sequence, i.e., at a position around 1000 bases down. For example, in the event that this target base sequence is the first 16s portion (array X) of the Mu50 strain shown in FIG. 5, this means that a base sequence unique to this array exists around 1000 bases down of the sequence X, which is a sequence different from other 16s portions on the Mu50 strain and different from the 16s rRNA from strains of *staphylococcus aureus* other than Mu50. Accordingly, selecting a probe candidate from this portion is unsuitable. Also, the portions with a low uniqueness in the upper graph indicate that the bacterium cannot be distinguished from other bacteria, so selecting a probe candidate from such portions is unsuitable.

Accordingly, a probe candidate is selected from a portion where the upper graph peaks (i.e., where uniqueness between different bacteria types is high) and where the lower graph does not peak (i.e., where uniqueness between different bacteria types is low). Thus, a probe can selected with high uniqueness (i.e., low frequency) regarding bacteria types other than the bacterium to be determined, and low uniqueness (i.e., high frequency) regarding various variations of the bacterium to be determined. That is to say, a user can easily select a suitable probe candidate by displaying multiple partial base sequences so as to compare the uniqueness of each, as shown in FIG. 8.

Consequently, a probe is selected which exhibits a strong hybridization reaction for the same bacterium regardless of the loci and strains of the 16s rRNA coding sequence contained in the hybridization solution, and which exhibits a weak hybridization reaction for different bacteria regardless of the loci and strains of the 16s rRNA coding sequence contained in the hybridization solution.

Note that the probe design method according to the present invention is not restricted to applications aimed at identifying infections. Rather, the method can be applied to any case wherein there is some degree of variation in a base sequence generally judged to be the same. For example, this may be applied to MHC widely used for individual identification of humans, and so forth.

Next, the probe set selecting step 109 shown in FIG. 1 will be described. The most simple probe set selection method is to take the probes which have yielded high evaluation marks in the probe evaluation step 108 in FIG. 1, make the length the same, and use as a probe set. However, generally, the hybridization reaction is determined by the melting temperature rather than the length of the probe base sequence. Accordingly, a probe set with higher quality can be obtained by setting a standard probe length n (n=24 in this example) for example, obtaining the melting temperature for each of the probes having a length within a predetermined range of this length (±2 in the present embodiment), and determining probes to be employed so that the melting temperature is as constant as possible.

Known methods for calculating the melting temperature of a base sequence include a method based on the mixture percentage of bases of the array, a method called the "nearest neighbor method" wherein the melting temperature is calculated from the array of two consecutive base sequences.

Also, in the event that the length of the base sequence exceeds 20, there are cases wherein secondary structures are formed, making the base sequence unsuitable for use as a probe. Accordingly, to avoid this, an arrangement may be made wherein probes which would readily form secondary structures are eliminated by calculating the probability of formation of secondary structures, using for example a method conceived by Michael Zuker, described in "Calculating Nucleic Acid Secondary Structure" (Current Opinion in Structural Biology, 10, 303-310 (2000)), or the like.

Also, the method using the frequency tables described in the probe evaluation step in FIG. 1 is a method for selecting probe candidates based on only the uniqueness, so the actually selected probe group may be made up of the same sort of base sequences. Accordingly, matching is preferably performed between the probe candidates to check how similar the candidates are, and eliminate similar probe candidates. For example, in the case of selecting a probe set from N probes, N(N−1)/2 candidates are matched, how similar the base sequences of the probes are is evaluated, and the probe set with the greater number of different bases is selected. This allows a high-quality probe set to be selected. This is known as a method for preventing so-called cross-hybridization.

[Detailed Description of Probe Design Device]

Figure 9:
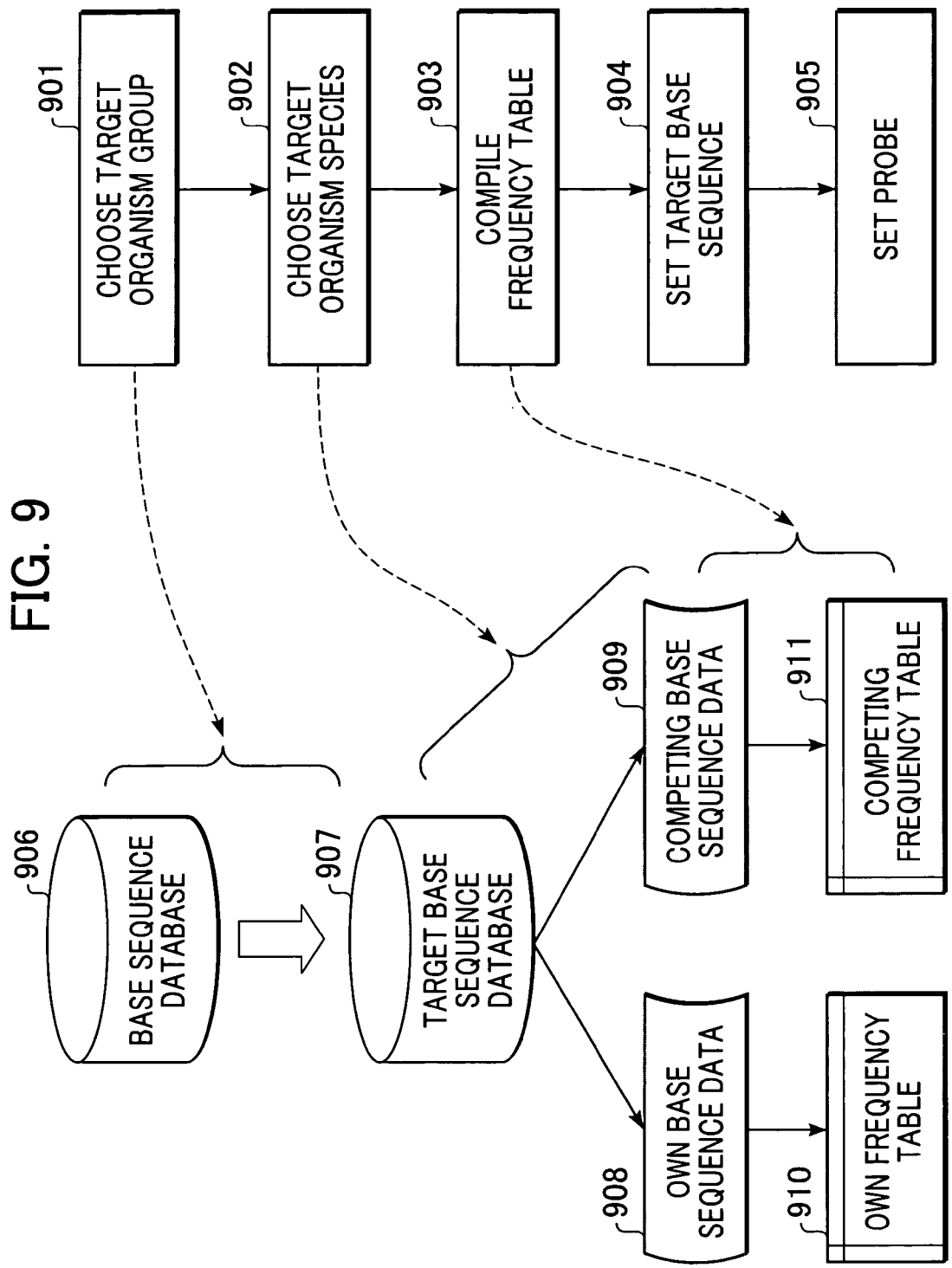
FIG. 9 is a flowchart describing the probe design method according to the first embodiment.

The flow of a probe design program according to the present embodiment will be described with reference to FIGS. 9 through 11. The flow of the probe design program starts with setting the target organism group (901). For example, in the case of designing a probe for determining the culprit bacterium of an infection, the target organism group is selected regarding genome information such as bacterium, virus, fungus, and the like, from a base sequence database 906. In FIG. 9, the base sequence database 906 is a base sequence data such as a public database, an example of which is that of the NCBI, a database architecture on an in-house intranet, or the like. The type or structure thereof is of little concern with regard to the present invention, what is crucial is that the greatest amount of currently-available data is stored therein. On the other hand, the target base sequence database 907 only includes the genome information of the species selected in the target organism group setting (901). For example, in the event that this program is applied to probe design for determining human constitution, the base sequence stored in the target base sequence database 907 is information for all alleles at DRB1 for MHC, and so forth.

Next, the target species is selected (902). Upon selecting the target species, the base sequences contained in the target base sequence database 907 is divided into own base sequence data and competing base sequence data. That is to say, own base sequence data 908 corresponding to multiple polymorphs and multiple genome loci of the target species is extracted from the information contained in the target base sequence database 907, and competing base sequence data 909 corresponding to multiple polymorphs and multiple genome loci of species other than the target species is extracted from the information contained in the target base sequence database 907.

Next, the own frequency table 910 (equivalent to the own frequency table 105 in FIG. 1) and competing frequency table 911 (equivalent to the competing frequency table 106 in FIG. 1) are created based on the selected target species (903). At the time of creating the frequency tables (903), normally, the targeted genome region is also set. For example, in the event of designing a probe to determine a bacterium, the portion of 16s rRNA may be selected.

More specifically, as shown in FIG. 4, the target nucleic acid is normally amplified by PCR when experimenting using DNA microarrays. At this time, only the regions between the PRC primers are amplified, so a frequency table is compiled using only the portions of the target base sequence database 907 amplified by PCR. In the event of applying the present program to probe design for determining human constitution, the target DNA region is set to a portion such as DRB1 of MHC for example, so there is no need to set this DNA region. Also, in the case of analyzing MHC DRB1, alleles up to three digits with no difference manifested in protein expression are handled as the same type. Note that the nucleic acid region to be targeted, or the PCR amplification region, is normally specified as a program property, and is not set each time through a user interface.

Next, the target base sequence is selected (904), the uniqueness of a partial sequence group of the target base sequence is evaluated using the own frequency table 910 and competing frequency table 911, and the probe is selected (905).

Figure 10:
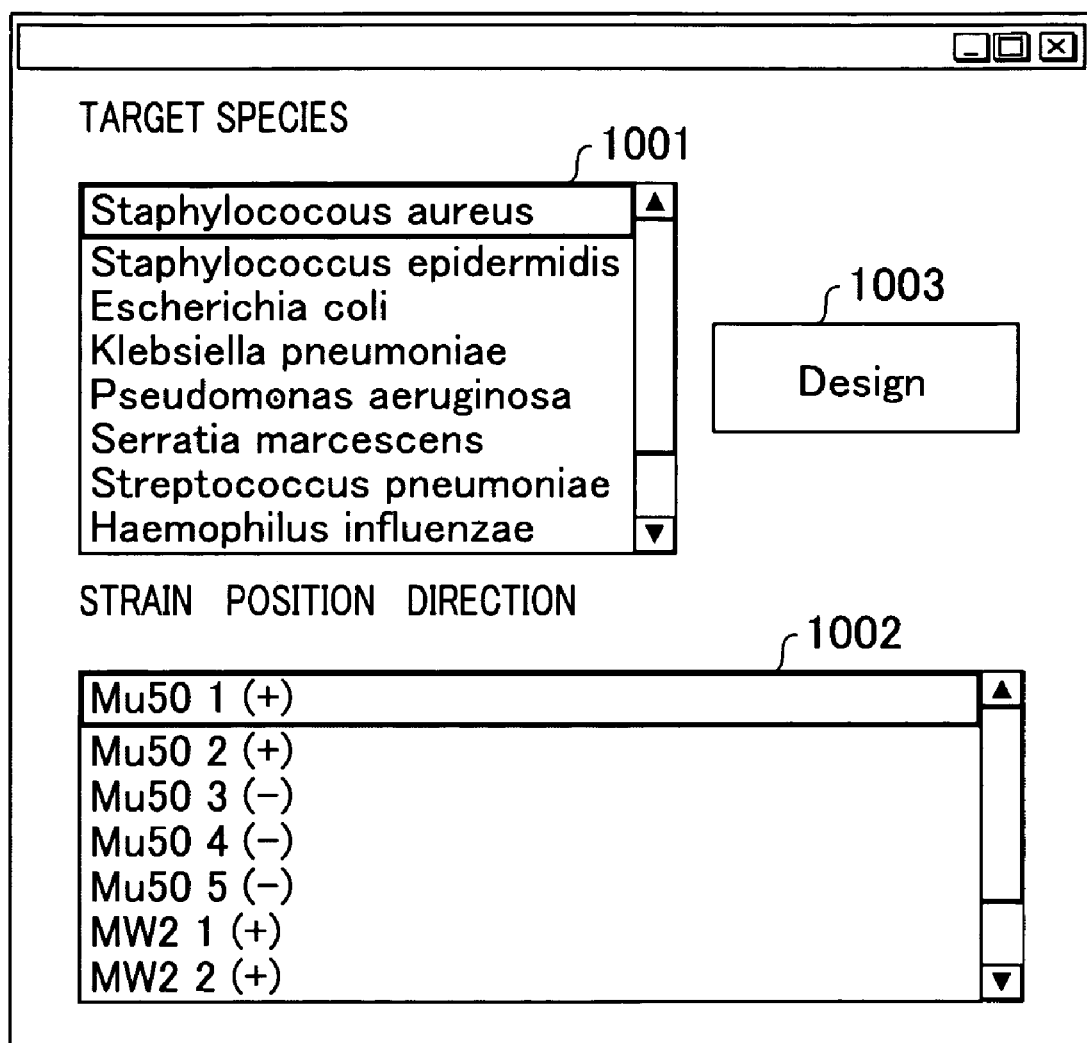
FIG. 10 is a diagram illustrating a user interface in the probe design method according to the first embodiment.

FIG. 10 illustrates an example of a user interface for making selections, from the target species (902) to the target base sequence (904). First, a list of bacteria is shown in a target bacterium type space 1001, from which a target bacterium is selected. Here, in the event that *staphylococcus aureus* is selected for example, a list is displayed of the base sequence for 16s rRNA of various loci of various strains of *staphylococcus aureus* in the strain display space 1002. In the interaction so far, 902 and 903 shown in FIG. 9 (i.e., selecting the target species and compiling the frequency tables) are executed.

The multiple polymorphic strains displayed in the strain display space 1002 are the strains shown in FIG. 5. The base sequences can be identified by displaying the name of the strain, position on genome, and direction, for example, as shown in FIG. 10.

Selecting one sequence from the list of base sequences in the strain display space 1002 executes selection of the target base sequence (904). In the event that the leading 16s rRNA of the Mu50 strain of *staphylococcus aureus* is selected as shown in FIG. 10, the sequence X shown in FIG. 5 is selected as the target base sequence. Pressing the design button 1003 brings up a design screen.

Figure 11:
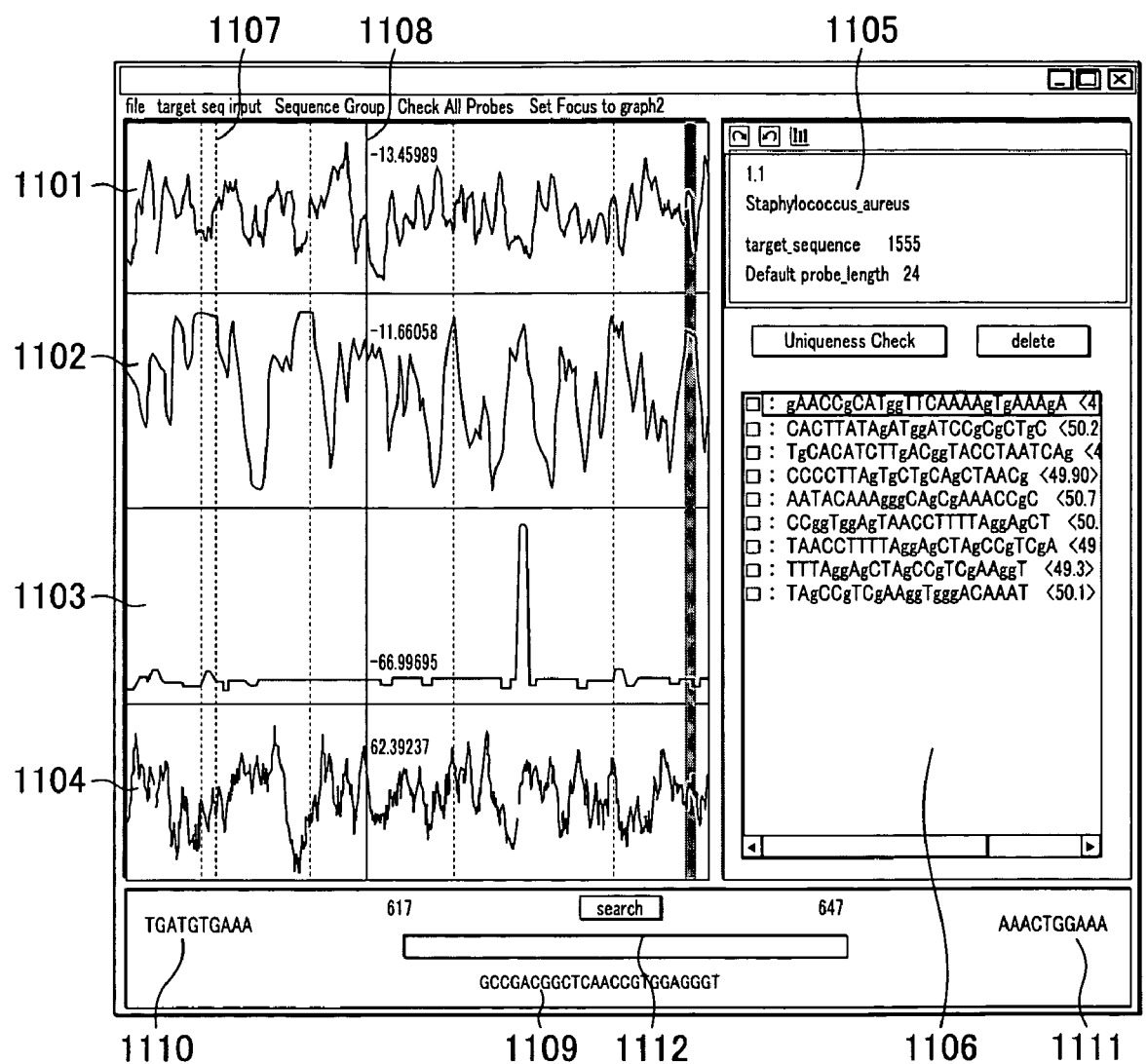
FIG. 11 is a diagram illustrating a user interface in the probe design method according to the first embodiment, showing SEQ ID NO:151 through SEQ ID NO:162.

FIG. 11 is a diagram illustrating an example of an actual design screen. Reference numerals 1101 through 1104 denote graphs, and the horizontal axis represents the position on the target base sequence selected with a user interface such as shown in FIG. 10 for example, with each graph showing the values for the partial base sequences at each position on the target base sequence. The graphs 1102 and 1103 correspond to the upper and lower graphs in FIG. 8, with the graph 1102 showing the uniqueness of the partial sequence at each position as to the competing base sequence data, and the graph 1103 showing the uniqueness of the partial sequence at each position as to the own base sequence data. Also, graph 1101 shows the uniqueness of the partial sequence at each position as to the human genome. Graph 1104 shows the melting temperature of base sequences of a predetermined number of bases (in this example, base sequences of 24 bases) starting at each position.

In the event of the user manually setting probes, each probe should be set at the areas where the graph 1102 peaks and the graph 1103 shows a trough, as shown in FIG. 8.

Reference numeral 1105 denotes an information space, for displaying the current target species and various parameters and the like. Note that the default base sequence length for the present embodiment is set to 24, and the melting temperature for the graph 1104 is calculated based on this.

Reference numeral 1106 denotes a list of design probes, the positions of which are displayed with a dotted line 1107. The solid line 1108 represents the "current" position, which is the position of interest as of now. The partial base sequence corresponding to that position (24-base base sequence is displayed in the space 1109, the base sequence immediately prior to that position is displayed in the space 1110, and the base sequence immediately following that position is displayed in the space 1111. With the present embodiment, the sequences of the 10 bases before and after are displayed. Also, the user interface shown in FIG. 11 has functions for searching for a base sequence from the target base sequence, as indicated by reference numeral 1112.

Also, the reason that the uniqueness of the partial sequence of the target base sequence as to the human genome is displayed as graph 1101 for example, is that human genes are contained in the process of designing probes for determining culprit bacteria for infections, although this display is not indispensable.

As described earlier with reference to the experiment procedure for designing a probe, the melting temperature (Tm) should be as close as possible among the selected probes. This is why the graph 1104 for example is displayed to show the Tm of the partial base sequence at that position.

In the probe evaluation step 108, the probe candidates are evaluated according to the movement of the solid line 1108 which the user has instructed with reference to the graphs 1101 through 1104. At this time, the user is notified in the event that the solid line has entered a settable position while being moved (portions where the graph 1103 shows uniqueness lower than a first threshold, and the graph 1102 shows uniqueness higher than a second threshold), by changing the color of the solid line 1108, for example. Thus, the user can find suitable base sequences more easily. Pressing an unshown OK button while the solid line 1108 is at this settable position sets the partial corresponding to this position as a probe candidate. The probe candidates thus set are further narrowed down in the probe set selecting step 109, thereby determining suitable probe sets.

Note that in the probe evaluation step 108, portions where the graph 1103 shows low uniqueness and the graph 1102 shows high uniqueness may be automatically extracted and presented to the user. For example, portions where the graph 1103 shows uniqueness lower than the first threshold and the graph 1102 shows uniqueness higher than the second threshold can be extracted and presented to the user.

Complementary sequences to the base sequences designed as described above can be used as probes in the same way, so these may be displayed alongside, or presented as design results.

Second Embodiment

With the first embodiment, the frequency information is displayed as shown in FIG. 11, so as to allow the user to select suitable positions. Using the frequency information in this way enables the user to easily select suitable probe candidates, but the number of probes set for microarrays is generally large, on the order of hundreds if not thousands. Accordingly, an arrangement wherein a user sets all of the probes based on frequency information can require a great amount of time and trouble. Also, as stated in the first embodiment, partial base sequences can be automatically extracted by simply comparing uniqueness values with threshold values. However, in this case, there are problems that (1) searching over the entire base sequence length requires a long time for calculations, (2) there is the possibility that a great number of similar base sequences may be extracted, and (3) there is a difficulty in extracting partial base sequences from positions suitably dispersed over the entire length of the base sequence.

Accordingly, with the second embodiment, an automatic method for probe design which solves these probes will be described. The configuration of the information processing device to which the probe design method according to the second embodiment is applied is the same as that of the first embodiment (FIG. 2).

Figure 12:
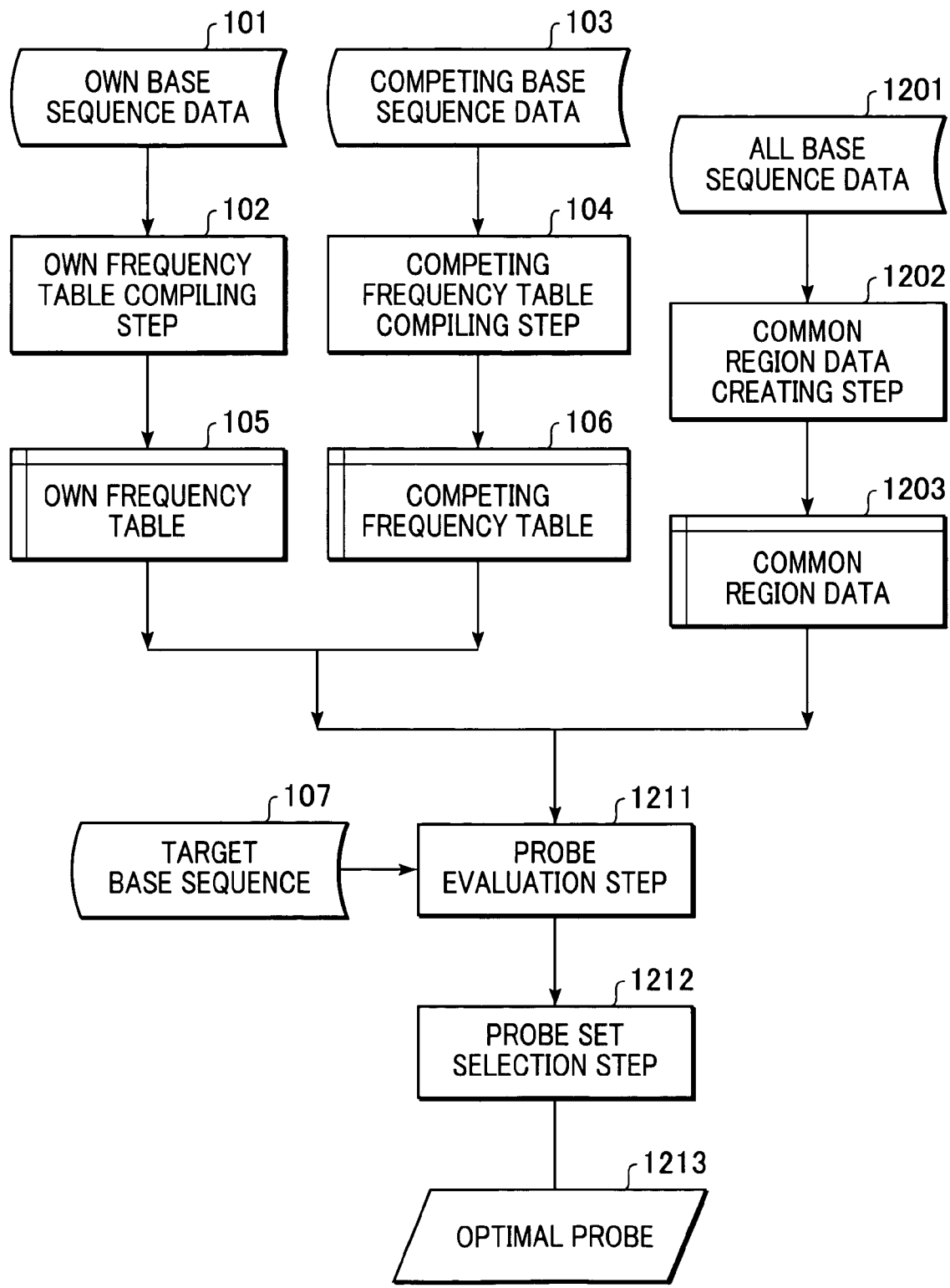
FIG. 12 is a diagram illustrating the overview of a probe design method according to a second embodiment.

FIG. 12 is a flowchart description of the procedures for the probe design method according to the second embodiment. The steps and data that are the same as those in the first embodiment (FIG. 1) are denoted with the same reference numerals.

Reference numeral 1201 denotes all base sequence data, which is a collection of the own base sequence data 101 and the competing base sequence data 103. Reference numeral 1202 denotes a common sequence data creating step for extracting partial sequences common to all base sequence data, and creating common sequence data 1203. The common partial base sequences are base sequences of a predetermined number of bases or longer (e.g., base sequences with a length of 20 bases or more), and are obtained by searching all base sequences.

Reference numeral 1211 denotes a probe evaluation step, which is a step for yielding probe candidates from the target base sequence 107 using the own frequency table 105 and competing frequency table 106. Reference numeral 1212 denotes a probe set selecting step, where a suitable probe set is selected from the probe candidates obtained as a result of the probe evaluation step 108. Reference numeral 1213 denotes the optimal probe ultimately obtained. Note that in the probe design processing shown in FIG. 12, input is the target base sequence 107, and output is the optimal probe 1213.

Now, automatic probe design according to the present embodiment will be described. With the present embodiment, the common region data 1203 is used for the automation of the probe design. The common region data 1203 is created in the common region data creating step 1202, where all base sequence data 1201, which is a collection of the own base sequence data 101 and the competing base sequence data 103, is searched for partial sequences common to all base sequences, and the position on the sequence and the length thereof are saved as common sequence data 1203. With the example of bacterial 16s rRNA, the common partial sequences are known to be at similar positions.

Figure 13:
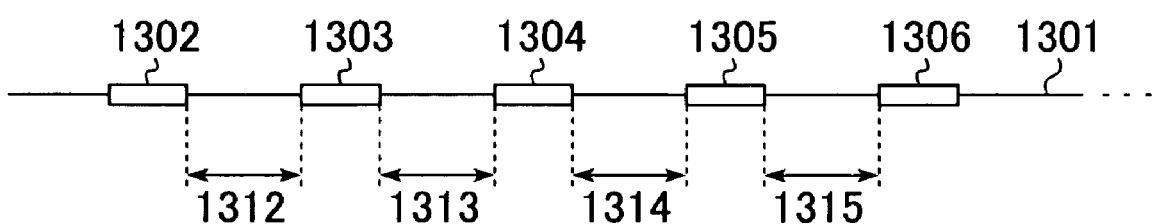
FIG. 13 is a diagram illustrating common regions on a target base sequence, and portions between the common regions.

Making reference the common sequence data 1203 with regard to the target base sequence data 107 allows the common regions 1302, 1303, and so on through 1306 and so forth, and the regions 1303, 1313 and so on through 1315 and so forth, between the common regions, to be distinguished on the target base sequence denoted by reference numeral 1301, as shown in FIG. 13. One position wherein the uniqueness between strains of the same bacterium is low and the uniqueness between different bacteria is high is selected by making reference to the own frequency table 105 and the competing frequency table 106 in the regions between the common regions. There are multiple common regions 1302 on the target base sequence 1301, and accordingly multiple regions 1303 between the common regions, so probes can be set over the entire length of the target base sequence 1301 by mechanically repeating the same process as long as there are unprocessed regions between the common regions. This processing can also be mechanically processed even in the event that there are a great number of target base sequences 110 over a range of multiple types of bacteria, and accordingly can be automated by a computer.

Note that, as in the first embodiment, the probe design method according to the present invention is not restricted to applications aimed at identifying infections. Rather, the method can be applied to any case wherein there is some degree of variation in a base sequence generally judged to be the same. For example, this may be applied to MHC widely used for individual identification of humans, and so forth.

Also, the common region data 109 created in the common sequence data creating step 106 can also be used as a universal primer for PCR, capable of amplifying in common a great number of types of genes.

[Detailed Description of Probe Design Device]

Figure 14:
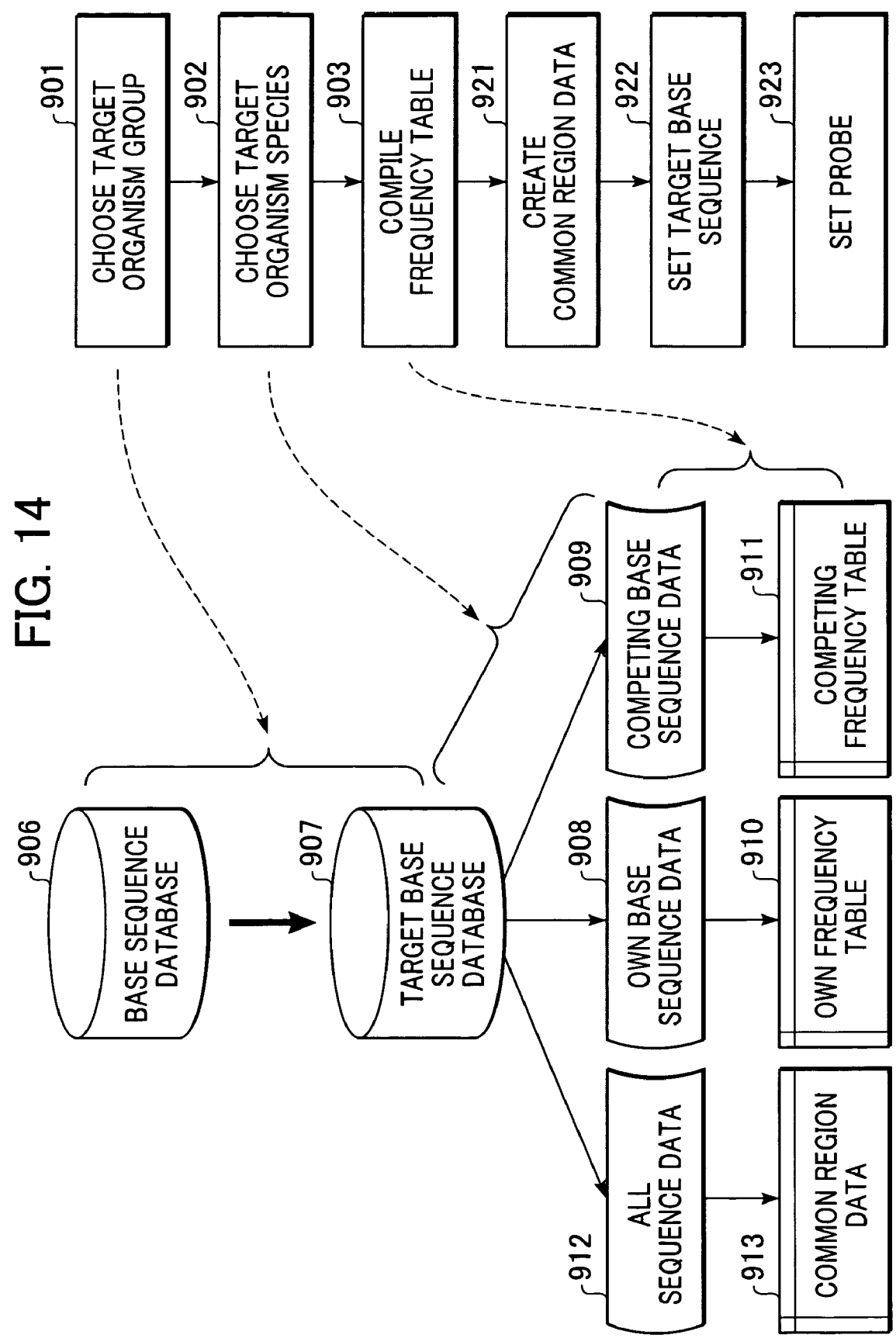
FIG. 14 is a flowchart describing the probe design method according to the second embodiment.

The flow of the probe design program according to the second embodiment will be described with reference to FIGS. 14 through 16. In FIG. 14, the processing and data that are the same as in the first embodiment (FIG. 9) are denoted with the same reference numerals. As described above with reference to FIG. 9, in the target organism group selection (901), genome information regarding, for example, bacterium, virus, fungus, and the like, belonging to a target organism group selected according to the probe to be designed, is selected from a base sequence database 906, and stored in the garget base sequence database 907.

Next, in selecting the target species (902), the base sequences contained in the target base sequence database 907 are divided into own base sequence data and competing base sequence data. That is to say, own base sequence data 908 corresponding to multiple polymorphs and multiple genome loci of the target species is extracted from the information contained in the target base sequence database 907, and competing base sequence data 909 corresponding to multiple polymorphs and multiple genome loci of species other than the target species is extracted from the information contained in the target base sequence database 907.

Next, the own frequency table 910 (equivalent to the own frequency table 105 in FIG. 1) and competing frequency table 911 (equivalent to the competing frequency table 106 in FIG. 1) are created based on the selected target species (903). At the time of creating the frequency tables (903), normally, the targeted genome region is also set. For example, in the event of designing a probe to determine a bacterium, the portion of 16s rRNA may be selected.

Also, common region data 913 (equivalent to the common region data 1203 in FIG. 12) is created (921) along with the frequency tables (903). Information of the partial sequences (common region data 912) shared between all base sequences (912) contained in the target base sequence database 907 is stored in a common region table 913. Compiling of the frequency tables is the same as described in the first embodiment.

Next, the target base sequence is selected (922), the uniqueness of a partial sequence group of the target base sequence is evaluated using the own frequency table 910 and competing frequency table 911, and the probe is selected (923).

Figure 15:
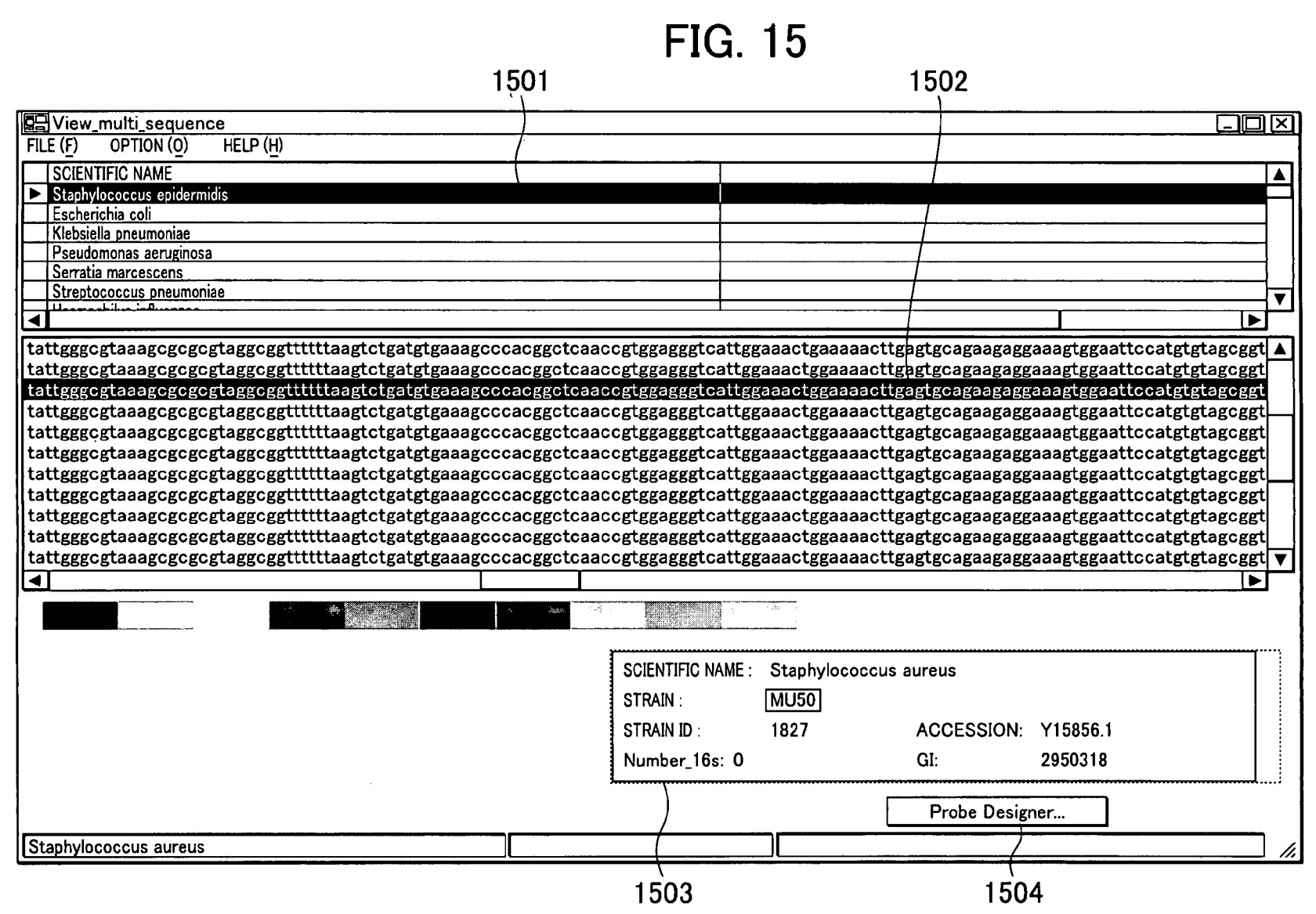

FIG. 15 illustrates an example of a user interface for making selections, from the target species (902) to the target base sequence (922). First, a list of bacteria is shown in a target bacterium type space 1501, from which a target bacterium is selected. Here, in the event that *staphylococcus aureus* is selected for example, a list is displayed of the base sequence for 16s rRNA of various loci of various strains of *staphylococcus aureus* in the strain display space 1502. In the interaction so far, 902, 903, and 921 shown in FIG. 14 (i.e., selecting the target species and compiling the frequency tables) are executed.

Each strain of *staphylococcus aureus* has multiple 16s rRNA regions as shown in FIG. 5, so information regarding the base sequence selected from the display space 1502 is displayed in a display space 1503 to enable selection of a 16s rRNA region from an optional locus of an optional strain. Displaying the strain name, information of position on the genome, and so forth, in the display space 1503 allows each base sequence to be identified. An arrangement may also be provided to display identification Nos. uniquely defined by public databases, such as GI or Accession No., and at the same time display information from the public database based on the identification No. in the display space 1503. Also, the base sequence display space 1502 may display multiple base sequences with the positions adjusted (by multiple alignment processing). Further, the base sequence display space 1502 may highlight the portions of the common regions between the base sequences by changing the color, font, or the like.

Selecting one sequence from the list of base sequences in the strain display space 1502 executes selection of the target base sequence (922). In the event that the leading 16s rRNA of the Mu50 strain of *staphylococcus aureus* is selected as shown in FIG. 15, the sequence X shown in FIG. 5 is selected as the target base sequence. Pressing the design button 1503 brings up a design screen such as shown in FIG. 16.

Figure 16:
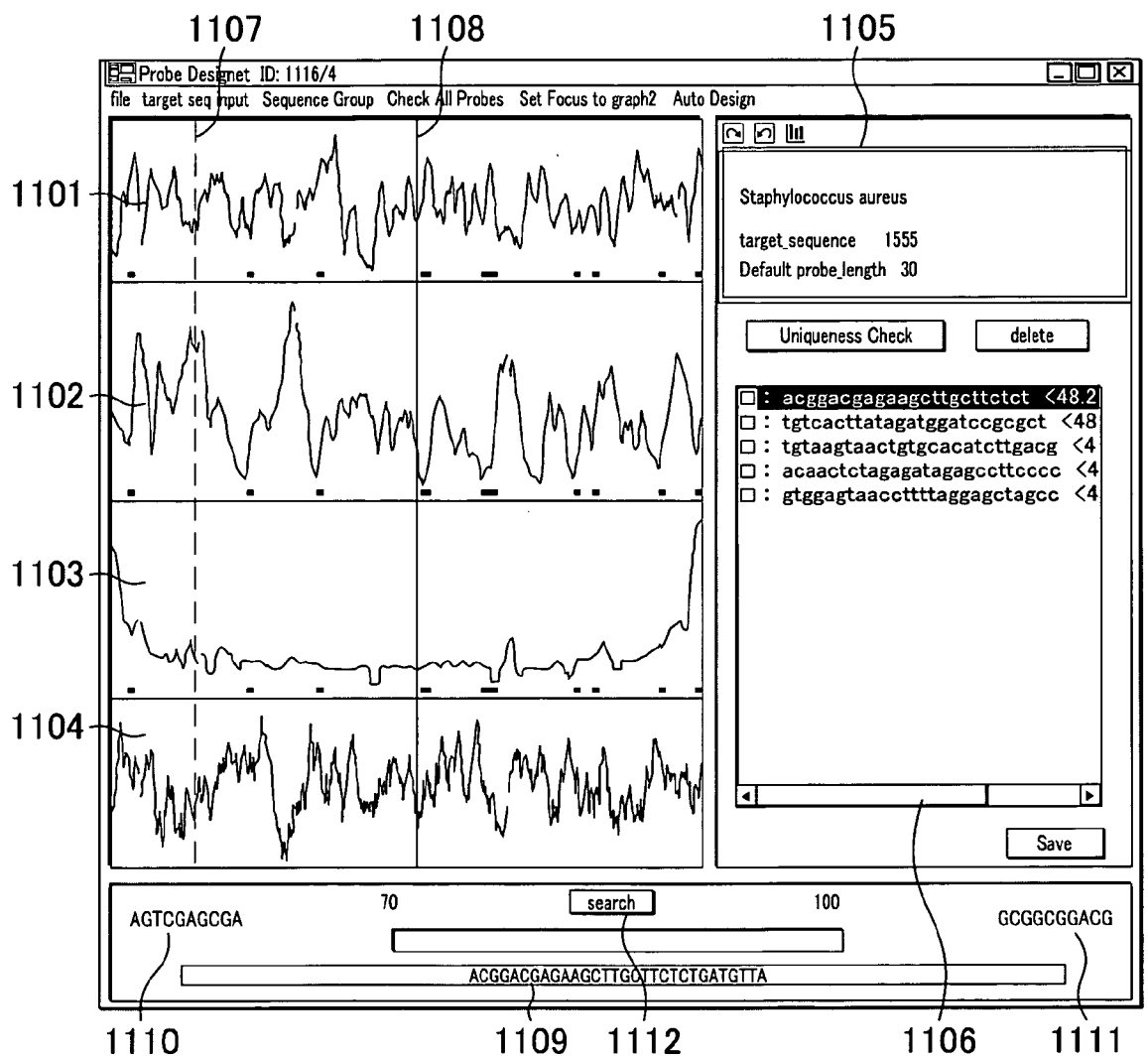
FIG. 16 is a diagram illustrating a user interface according to the second embodiment, showing SEQ ID NO:163 through SEQ ID NO:170.

FIG. 16 illiterates an example of a design screen according to the preset embodiment. The interface configuration is approximately the same as in the first embodiment (FIG. 11), and the same components are denoted with the same reference numerals. Reference numerals 1101 through 1104 denote graphs, and the horizontal axis represents the position on the target base sequence selected with a user interface, such as shown, for example, in FIG. 15. As described with reference to FIG. 11, the graphs 1102 and 1103 correspond to the upper and lower graphs in FIG. 8, with the graph 1102 showing the uniqueness of the partial sequence at each position as to the competing base sequence data, and the graph 1103 showing the uniqueness of the partial sequence at each position as to the own base sequence data. Also, graph 1101 shows the uniqueness of the partial sequence at each position as to the human genome. Graph 1104 shows the melting temperature of base sequences of a predetermined number of bases (in this example, base sequences of 24 bases) starting at each position.

As described earlier, in the event that a target base sequence is selected with a user interface such as shown in FIG. 15, automated probe design can be performed using the own frequency table 910 and competing frequency table 911 and common region table 913. In this case, probes that have already been created are displayed in the design screen shown in FIG. 16, and the user can edit the probe position (including adding and deleting).

Points 1601 shown in the graphs 1101, 1102, and 1103, illustrate the position of the common region data 913 obtained from the common region table 912 shown in FIG. 14. In each of the regions between the points 1114 indicating the common regions, the areas where the graph 1102 peaks and the graph 1103 shows a trough are automatically selected, thereby automatically setting probes.

A manual mode may be provided wherein a user manually sets probes (i.e., specifies partial base sequences. In this manual mode, probes should be specified at portions where the graph 1102 peaks and the graph 1103 shows a trough, as described in the first embodiment (FIG. 8 or FIG. 11). In this case, an arrangement may be made wherein the head of the partial base sequences cannot be specified in common regions indicated by the points 1601.

Reference numeral 1105 denotes an information space, for displaying the current target species, various types of parameters, and so forth. Note that 24 is set as the default base length with the present embodiment, and the melting temperature is calculated for the graph 1104 based on this. Reference numeral 1106 denotes a list of designed probes, with the position thereof being displayed by a dotted line 1107. The solid line 1108 represents the "current" position, which is the position of interest as of now. The partial base sequence corresponding to that position (24-base base sequence) is displayed in the space 1109, the base sequence immediately prior to that position is displayed in the space 1110, and the base sequence immediately following that position is displayed in the space 1111. With the present embodiment, the sequences of the 10 bases before and after are displayed.

Also, complementary sequences to the base sequences designed above can also be used as probes in the same way, so it is needless to say that these may be also be displayed alongside, or may be presented as design results.

Upon a search button 1112 being pressed, the flow begins searching, to extract partial base sequences suitable for probes from the target base sequence. As described earlier, with the second embodiment, the partial base sequences are searched using own frequency information, competing frequency information, and common region information, are used for automatic probe design. The following is a further detailed description of the automated probe design method according to the present embodiment, with reference to FIG. 17.

Figure 17:
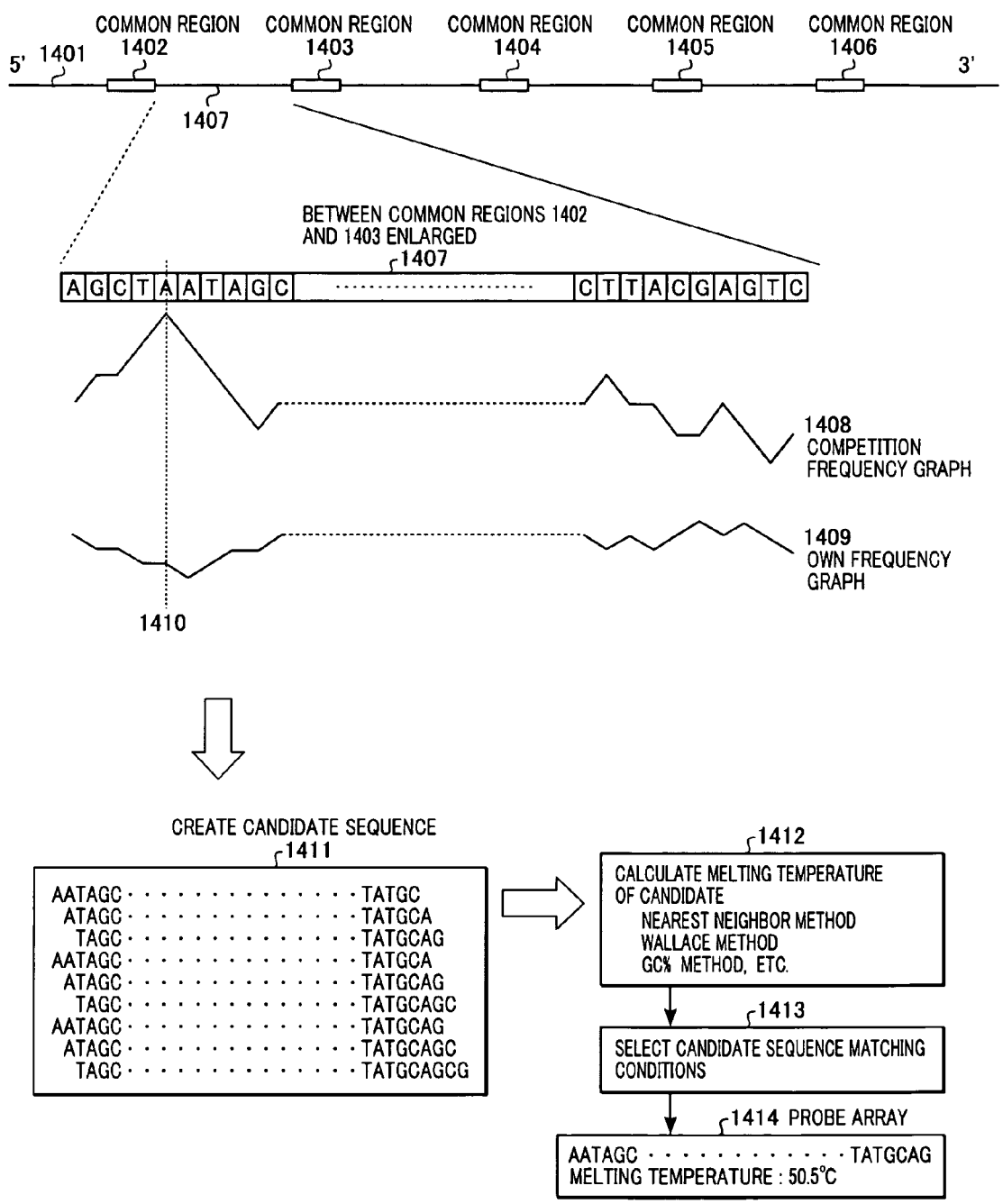
FIG. 17 is a diagram illustrating an automatic probe design method according to the second embodiment.

FIG. 17 illustrates an example of creating a probe for an infecting organism, under the conditions of 24 ±2 in probe length and 50 ±1° C. in melting temperature.

In a case wherein there are five common regions, 1402 through 1406, on the target base sequence 1401, first, a probe will be created for between the common regions 1402 and 1403, i.e., the region denoted by 1407. Regardless of whether the probe between the common regions 1402 and 1403 is successfully created, next, a probe is created for between the common regions 1403 and 1404 in the same way, followed by the common regions 1404 and 1405, and then the common regions 1405 and 1406, so probe fabrication is attempted in sequence at all regions between the common regions.

The procedures for attempting to create a probe are as follows. In the region 1407 between common regions, a position 1410 where the indicator of the uniqueness regarding the base sequence of another species obtained from the competing frequency graph 1408 is the highest, and the indicator of the uniqueness as to the base sequence of the same species obtained from the own frequency graph 1409 is low is extracted, and a partial sequence group 1411 serving as candidates for checking the melting temperature is created based on that position. With the present embodiment, in the event that a position wherein the indicator indicating uniqueness as to the base sequence of another species has been detected, and the indicator indicating uniqueness as to a base sequence of the same species is lower than a predetermined value, this is taken to mean that extraction of a candidate position has succeeded. In the event of failing to extract a candidate position, the processing moves on to the next region. There, a partial base sequence 24 bases long is extracted from the target base sequence with the candidate position 1410 as the head thereof. Next, in the candidate sequence creating 1411, one or two bases are added to and/or deleted from one or both of the head and end of the partial sequence obtained based on the position 1410 as the head, thereby creating multiple candidate partial base sequences having variations in the start position, end position, and base sequence length. Then, in 1412, the melting temperature for each of the multiple partial sequences obtained in 1411 is calculated. In 1413, a sequence which is within the range of the assumed temperature (50° C.±1° C. in the present embodiment) and also closest to the assumed temperature (50° C. in the present embodiment) is extracted. Thus, a probe 1414 can be obtained in the region 1407 between the common region 1402 and the common region 1403. In the event that the results of calculating the melting temperature regarding the multiple partial sequences obtained in 1411 indicates hat none satisfy the melting temperature conditions, creating of a probe between the common region 1402 and the common region 1403 is abandoned, and next, probe fabrication is attempted at the region between the following common region 1403 and the common region 1404.

Figure 18:
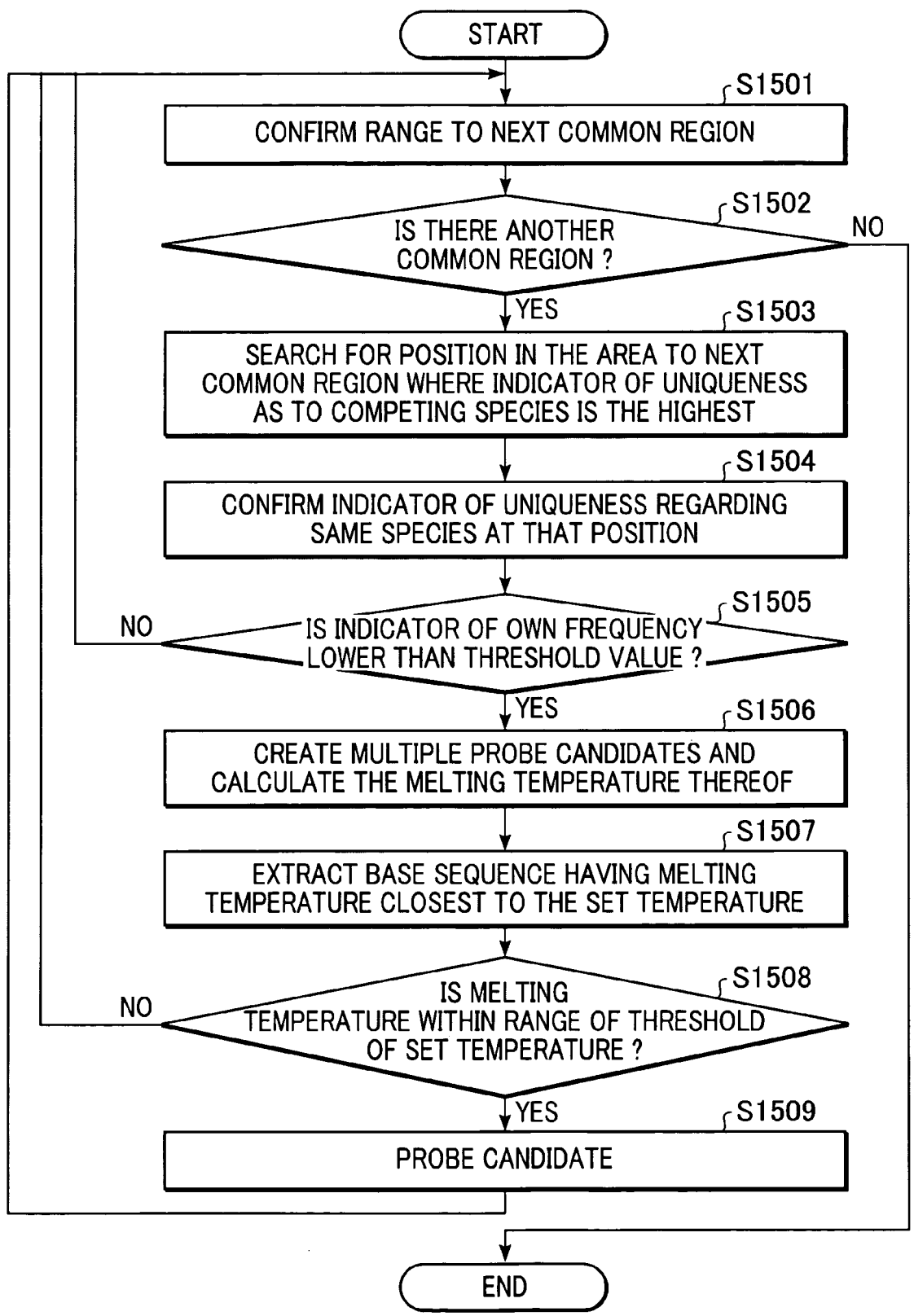
FIG. 18 is a flowchart illustrating the automatic probe design method according to the second embodiment.

FIG. 18 is a flowchart illustrating what has been described with reference to FIG. 17. FIG. 18 illustrates the procedures following selection of the nucleic acid sequence of the target gene, for automatically selecting probes from the nucleic acid sequence. The flowchart shown in FIG. 18 will be described with an example of creating a probe for 16s rRNA of an infecting organism, under the conditions of 24 ±2 in probe length and 50 ±1° C. in melting temperature.

First, common regions are searched for on the nucleic acid sequence of the target gene, from the 5' end toward the 3' end (S1501). In the event that a common region does exist (S1502), reference is made to the competing frequency table while shifting between the from the 5' end side up to the first common region of the target gene, and the position of a partial sequence where the uniqueness is the highest is found (S1503). Next, the uniqueness of this position as to the base sequence of the same species is checked with reference to the own frequency table (A1504), to see whether or not the uniqueness as to the base sequence of the same species is determined to be sufficiently low. The standard for determining whether the uniqueness is "sufficiently low" should be determined beforehand, according to the situations, such as, for example, being lower than an average value of the values of the own frequency table, lower than a preset optional frequency, or the like, in the event that the uniqueness as is determined to be high as to the base sequence of the same species as well, the flow returns to 1501, and whether or not a common region exists after the current position, i.e., in the direction of the 3' side, is determined. In the event that the value of the uniqueness from the own frequency table is determined to be sufficiently low in step S1505, partial base sequences 22 to 26 long are created by adding bases before and after the current position which serves as a reference (1411 in FIG. 17), and the melting temperature is calculated for each of the created base sequences (S1506). A base sequence which is the closest in melting temperature to 50° C. is selected, and in the event that the melting temperature is within the range of 49° C. to 51° C., this base sequence is taken as a probe (S1507 through S1509). In the event that the melting temperature is not within the range of 49° C. to 51° C., the flow returns to S1501, and whether or not a common region exists after the current position, i.e., in the direction of the 3' side, is determined.

Thus, the uniqueness of each portion section by common regions is calculated for the entire target base sequence, and the melting temperature, thereby creating a probe set distributed over the entire target base sequence.

[Probe Set Design Example and Experiment Example]

Figure 19:
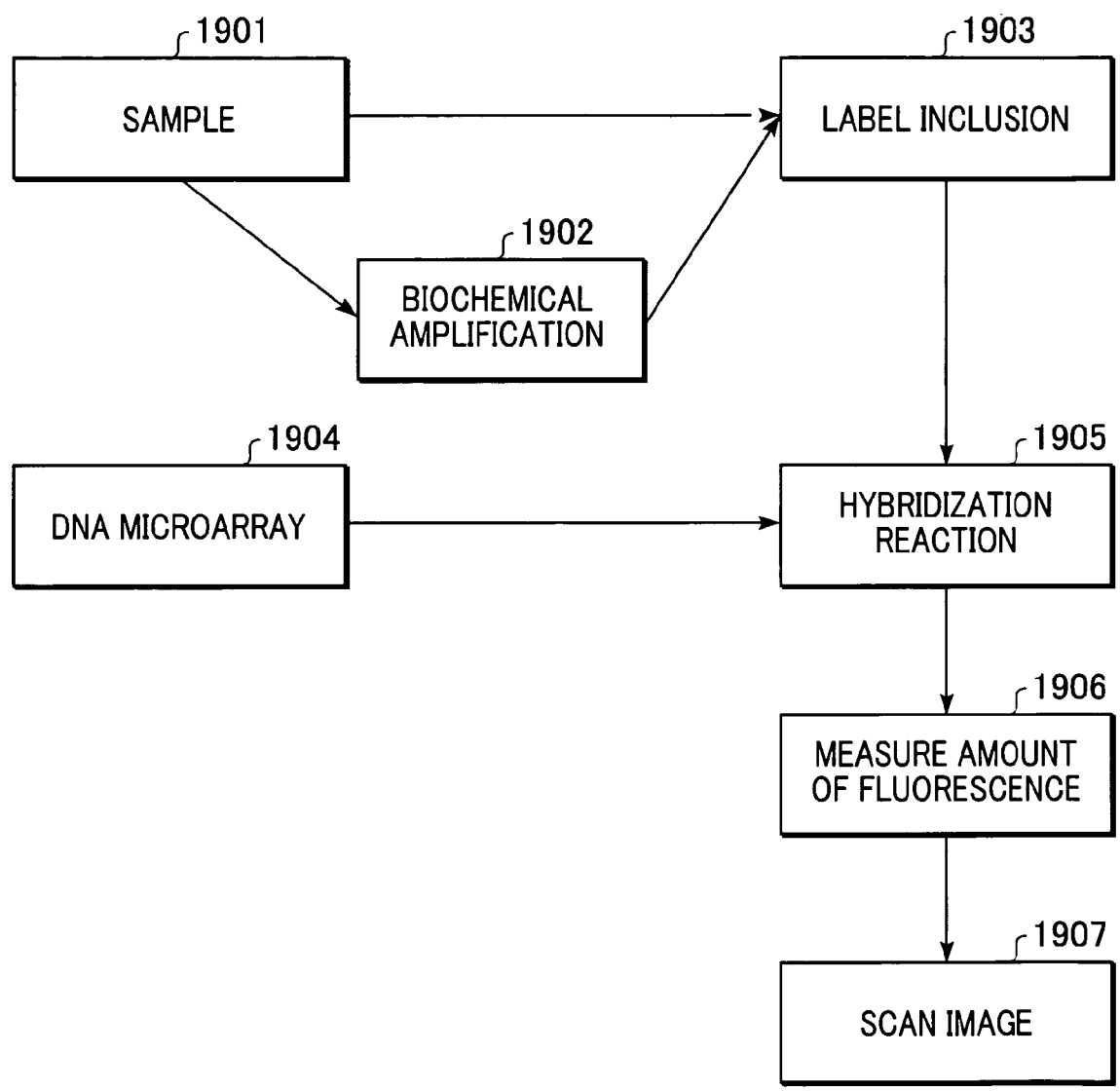
FIG. 19 is a diagram describing the procedures for performing nucleic acid analysis using the probe designed with the probe design method according to the embodiment.

Next, the experiment procedures for a DNA microarray using the probe designed using the probe design method according to the above-described embodiment will be described with reference to FIG. 19.

The "sample" 1901 here is a fluid or solid which is expected to contain the subject nucleic acid. For example, in the event of determining a causative organism of an infection, anything which may contain bacteria, including body fluids such as blood, spinal fluid, phlegm, stomach fluid, vaginal discharge, and oral mucous, and excrement such as urine or feces, from human or animal sources, can serve as a sample. Further, food which may contain organisms causing food poisoning or other contaminating organisms, environmental water such as drinking water and bathwater, filters from air and water cleaners, and so forth, i.e., anything which may be a medium contaminated with the bacteria, can be used as a sample. Moreover, plants and animals passing through quarantine for import/export are also subject to being samples.

Next, the sample 1901 is amplified using a "biochemical amplification" method (1902). In the case of pinpointing a culprit bacterium for an infection for example, the nucleic acid at issue may be amplified by PCR using a PCR reaction primer designed for detecting 16s rRNA, or further performing PCR reactions based on the PCR amplifications, or the like, and thus prepared. Also, the preparation may be made by amplification methods other than PCR, such as LMAP or the like.

Subsequently, the sample amplified by the biochemical amplification 1902, or the sample 1901 itself, is labeled with any of a number of labeling methods for visualization (label mixing 1903). A commonly-used labeling substance is a fluorescent substance such as Cy3, Cy5, Rodamin, or the like. Also, there are cases wherein labeling molecules are mixed in the biochemical amplification 1902.

The nucleic acid with the labeling molecules thus added is subjected to hybridization reaction with a DNA microarray 1904 (1905). This is as shown in FIG. 3. In the case of determining a culprit bacterium for an infection for example, the DNA microarray 1904 comprises a probe unique to a bacterium which has been fixed to a substrate. Now, probes corresponding to various bacteria are designed from the genome portion coding 16s rRNA for example, as described above. The carrying member (substrate) to which the probes of the DNA microarray 1904 are to be fixed to may be a flat substrate such as a glass substrate, plastic substrate, silicon wafer, or the like. Or, this may be a three-dimensional structure with an uneven shape, a spherical shape such as a bead, or a rod-like, string-like, or thread-like article. It should be noted that the form of the substrate or carrying member does not affect the embodiment or the advantages of the present invention in any way.

Normally, a substrate is used having a surface processed such that the probe DNA can be fixed thereto. Particularly, articles to which a functional group has been introduced to enable chemical reaction with the surface is a preferable arrangement from the point of reproducibility, since the probes are fixed thereto in a stable manner through the hybridization reaction process. The fixing method used with the present embodiment is an example using a combination of maleimide and thiol (—SH). That is to say, by bonding the thiol (—SH) group to the end of the nucleic acid probe, and processing the substrate such that the solid-phase surface has the maleimide group allows the thiol group of the nucleic acid probe supplied to the solid-phase surface and the maleimide group at the solid-phase surface to react, thereby fixing the nucleic acid probes. As a method for introducing the maleimide group, first, the surface of a glass substrate is made to react with an amino-silane coupling agent, following which the maleimide group is introduced by reaction with the amino group and an EMCS reagent (N-(6-Maleimidocaproyloxy)succinimide, manufactured by Dojindo Molecular Technologies, Inc.). Introduction of the SH group to the DNA can be performed by using 5'-Thiol-Modifier C6 (manufactured by Glen Research Corporation) at the time of synthesizing DNA with an automatic DNA synthesizer. Examples of the combination for the functional group besides the above-described combination of maleimide and thiol include a combination of epoxy group (on the solid-phase) and amino group (on the end of the nucleic acid probe). Further, surface processing by various types of silane coupling agents is also effective, and oligonucleotide having been introduced with a functional group, capable of reacting with the functional group introduced by the silane coupling agent, is used. A further method is to coat with a resin having a functional group.

Following performing the hybridization reaction 1905, the surface of the DNA microarray 1904 is washed, the nucleic acid not bonded to the probe is removed, the DNA microarray is then usually dried, following which the amount of fluorescence of the hybridization reaction 1905 is measured. Here, excitation light is irradiated into the substrate of the DNA microarray 1904, thereby obtaining an image wherein the intensity of fluorescence is measured (1906, 1907).

The following is a description of specific experiment procedures for the flow of an experiment intended to determine a causative bacterium of an infection described with reference to FIG. 19. It should be noted that the organism type determining method according to the present invention is not restricted to determining culprit bacteria of infections which is described below, but also may be used to determine human constitution with MHC or the like, or may be used for DNA or RNA analyses with regard to diseases such as cancer.

<1. Preparing Probe DNA>

Nucleic acid sequences (I–n) wherein (n is a number) of sequence Nos. 59 through 65 were designed as *enterobacter cloacae* strain detecting probes. Specifically, the above-described method was used to design the probes from genome portions coding 16s rRNA, using the NCBI database.

A thiol group was introduced to the 5' end of the nucleic acid of the probes with sequence Nos. 59 through 65 (complementary strand sequence Nos. 137 through 143) following synthesizing, according to method, so as to serve as a functional group for fixing to the DNA micro array. Introduction of the functional group was followed by purification and freeze-drying. The freeze-dried probe was kept in a freezer at –30° C.

The following probe sets were designed by the same method for *staphylococcus aureus, staphylococcus epidermidis, escherichia coli, klebsiella pneumoniae, pseudomonas aeruginosa, serratia marcescens, streptococcus pneumoniae, haemophilus influenzae*, and *enterococcus faecalis*.
*Staphylococcus aureus:* Sequence Nos. 1 through 9 (Sequence Nos. 79 through 87 for complementary strand)
*Staphylococcus epidermidis:* Sequence Nos. 10 through 16 (Sequence Nos. 88 through 94 for complementary strand)
*Escherichia coli:* Sequence Nos. 17 through 23 (Sequence Nos. 95 through 101 for complementary strand)
*Klebsiella pneumoniae:* Sequence Nos. 24 through 29 (Sequence Nos. 102 through 107 for complementary strand)
*Pseudomonas aeruginosa:* Sequence Nos. 30 through 37 (Sequence Nos. 108 through 115 for complementary strand)
*Serratia marcescens:* Sequence Nos. 38 through 43 (Sequence Nos. 116 through 121 for complementary strand)
*Streptococcus pneumoniae:* Sequence Nos. 44 through 50 (Sequence Nos. 122 through 128 for complementary strand)
*Haemophilus influenzae:* Sequence Nos. 51 through 58 (Sequence Nos. 129 through 136 for complementary strand)
*Enterococcus faecalis:* Sequence Nos. 66 through 72 (Sequence Nos. 144 through 150 for complementary strand)

<2. Preparing the Specimen Amplifying PCR Primer>

The nucleic acid sequences shown in Table 1 below were designed as 16s rRNA nucleic acid (target nucleic acid) amplifying PCR primers, for detecting infecting bacteria. Specifically, a probe set for specifically amplifying the part of the genome coding the 16s rRNA, i.e., primers where the specific melting temperature is matched as much as possible at both end portions of the 16s rRNA coding region of approximately 1500-base length strands were designed. Note that multiple types of primers were designed so that mutation strains, and multiple 16s rRNA coding regions on the genome, could be amplified at the same time.

TABLE 1

|  | Primer No. | Sequence |
|---|---|---|
| Forward Primer | F-1 | 5' GCGGCGTGCCTAATACATGCAAG 3' |
|  | F-2 | 5' GCGGCAGGCCTAACACATGCAAG 3' |
|  | F-3 | 5' GCGGCAGGCTTAACACATGCAAG 3' |
| Reverse Primer | R-1 | 5' ATCCAGCCGCACCTTCCGATAC 3' |
|  | R-2 | 5' ATCCACCCGCAGGTTCCCCTAC 3' |
|  | R-3 | 5' ATCCAGCCGCAGGTTCCCCTAC 3' |

Following synthesizing, the primers shown in Table 1 were purified by High Performance Liquid Chromatography (HPLC), with three types of forward primer and three types of reverse primer mixed, and dissolved in a TE buffering solution so that the concentration of each primer eventually is 10 pmol/μl.

<3. Extracting *Enterobacter Cloacae* Genome DNA (Model Specimen)>

(3-1. Culturing Microorganism and Pre-Processing for Genome DNA Extraction)

A standard strain of *enterobacter cloacae* was cultured according to method. 1.0 ml ($OD_{600}$=0.7) of this culture was taken in a micro-tube with a 1.5 ml capacity, and the bacteria were recovered by centrifugation (8500 rpm, 5 minutes, 4° C.). The supernatant was discarded, following which 300 μl of an enzyme buffer (50 mM Tris-HCl: pH 8.0, 25 mM EDTA) was added, and re-suspended using a mixer. The re-suspended bacteria fluid was recovered again by centrifugation (8500 rpm, 5 minutes, 4° C.). The supernatant was discarded, the above enzyme solution was added to the recovered bacteria, and re-suspended using a mixer.

Lysozyme 50 µl (20 mg/ml in enzyme buffer)

N-acetylmuramidase SG50 µl (0.2 mg/ml in enzyme buffer)

Next, the bacteria fluid to which the enzyme solution was added and re-suspended was left standing in a 37° C. incubator for 30 minutes, to dissolve wall cells.

(3-2. Genome Extraction)

Extracting of the genome DNA of the microorganisms was performed using a nucleic acid purifying kit (MagExtractor-Genome, manufactured by Toyobo Co., Ltd.). Specifically, first, 750 µl of a dissolution and adsorption fluid and 40 µl of magnetic beads were added into the microorganism suspension fluid prepared beforehand, and vigorously stirred for 10 minutes using a tube mixer (step 1).

Next, a micro-tube was set to a separating stand (Magical Trapper), left standing for 30 seconds to collect the magnetic particles on the wall of the tube, and the supernatant was discarded while set on the stand (step 2). 900 µl of a washing fluid was added, and mixed with a mixer around 5 seconds to re-suspend (step 3).

Next, a micro-tube was set to a separating stand (Magical Trapper), left standing for 30 seconds to collect the magnetic particles on the wall of the tube, and the supernatant was discarded while set on the stand (step 4). The steps 3 and 4 were repeated and the second washing (step 5) was performed, following which 900 µl of a 70% ethanol solution was added, and mixed with a mixer around 5 seconds to re-suspend (step 6).

Next, a micro-tube was set to a separating stand (Magical Trapper), left standing for 30 seconds to collect the magnetic particles on the wall of the tube, and the supernatant was discarded while set on the stand (step 7). The steps 6 and 7 were repeated and the second washing with the 70% ethanol solution (step 8) was performed, following which 100 µl of purified water was added to the recovered magnetic particles, and mixed with a tube mixer for 10 minutes.

Next, a micro-tube was set to a separating stand (Magical Trapper), left standing for 30 seconds to collect the magnetic particles on the wall of the tube, and the supernatant was collected in a new tube while set on the stand.

(3-3. Inspecting the Collected Genome DNA)

The genome DNA of the microorganism (*enterobacter cloacae* strain) collected was subjected to agarose electrophoresis and 260/280 nm light absorption measurement, thereby inspecting the quality (amount of low-molecular nucleic acid contained and degree of decomposition) and amount collected according to the method.

With this experiment, approximately 10 µg of genome DNA was collected, with no degradation of the genome DNA or inclusion of rRNA observed. The collected genome DNA was dissolved in a TE buffering fluid to a final concentration of 50 ng/µl, and used in the following experiment.

<4. Fabricating the DNA Microarray>

(4-1. Washing Glass Substrate)

A synthetic quartz glass substrate (25 mm by 75 mm by 1 mm in size, manufactured by IIYAMA TOKUSHU GLASS) was placed in a heat-resistant and alkali-resistant rack, and immersed in an ultrasound cleansing fluid prepared to a predetermined concentration. Following immersion overnight in the cleansing fluid, ultrasound cleansing was performed for 20 minutes. Next, the substrate was removed, lightly rinsed with purified water, and then subjected to ultrasound cleansing for 20 minutes in ultrapure water.

Next, the substrate was immersed for 10 minutes in a 1N sodium hydroxide solution heated to 80° C. Purified water cleansing and ultrapure water cleansing were repeated, thereby preparing a quartz glass substrate to serve as a DNA chip.

(4-2. Surface Processing)

A silane coupling agent KBM-603 (manufactured by Shin-Etsu Chemical Co., Ltd.) was dissolved in purified water to a concentration of 1%, and stirred for 2 hours at room temperature. Next, the glass substrate washed previously was immersed in the silane coupling agent solution, and left standing for 20 minutes at room temperature. The glass substrate was then removed, the surface thereof was lightly washed with pure water, and then dried by blowing nitrogen gas on both faces of the substrate. Next, the dried substrate was baked for 1 hour in an oven heated to 120° C., thereby completing the coupling agent processing, and amino groups were introduced to the substrate surface. Next, N-(6-Maleimidocaproyloxy)succinimide, manufactured by Dojindo Laboratories (hereafter abbreviated as "EMCS") was dissolved in a mixed solvent of equal amounts of dimethyl sulfoxide and ethanol, so that the final concentration was 0.3 mg/ml, thereby preparing an EMCS solution. The glass substrate was allowed to cool following baking, and immersed in the prepared EMCS solution for 2 hours at room temperature. Due to this processing, the amino group introduced to the surface of the substrate by the silane coupling agent and the succinimide group of the EMCS react, thereby introducing the maleimide group to the surface of the glass substrate. The glass substrate removed form the EMCS solution was washed using the mixed solvent in which the MCS was dissolved as stated above, then further cleansed with ethanol, and dried in a nitrogen atmosphere.

(4-3. Probe DNA)

The microorganism detecting probes fabricated in the experiment step 1 were dissolved in purified water, dispensed so that the final concentration (at the time of ink dissolution) was 10 µM for each. Subsequently, freeze-drying was performed to remove moisture.

(4-4. Discharging DNA Employing BJ Printer, and Bonding to Substrate)

An aqueous solution was prepared containing 7.5 percent by weight of glycerin, 7.5 percent by weight of thioglycol, 7.5 percent by weight of urea, and 1.0 percent by weight of acetynol EH (manufactured by Kawaken Fine Chemicals Co., Ltd.). Next, the seven types of probes previously prepared shown in Table 1 were dissolved in the mixed solvent so as to reach a stipulated concentration. The obtained DNA solution is filled in an ink tank for a bubble-jet printer (BJF-850, Manufactured by CANON KABUSHIKI KAISHA), which was mounted on a printing head.

The bubble-jet printer used here has been modified so as to enable printing onto a flat plate. Also, this bubble-jet printer can perform spotting at around a 120 µm pitch, 5 pl of DNA solution per spot, by inputting a printing pattern according to a predetermined file creating method.

Next, the modified bubble-jet printer was used to print on one glass substrate, and fabricate an array. Following confirmation that the printing was suitable, the substrate was left standing in a humidifier chamber for 30 minutes, so that the maleimide group on the surface of the glass substrate and the thiol group at the end of the nucleic acid probes react.

(4-5. Cleansing)

Following reaction for 30 minutes, the DNA solution remaining on the surface was washed off with 10 mM of a phosphate buffer solution (pH 7.0) containing 100 mM of NaCl, thereby yielding a DNA microarray with single-strand DNA fixed to the surface of the glass substrate.

<5. Amplification and Labeling of Specimen (PCR Amplification and Fluorescent Label Inclusion)>

The amplification and labeling reactions of the microorganism DNA serving as the specimen are shown below.

| | |
|---|---|
| Premix PCR reagent (TAKARA ExTaq) | 25 μl |
| Template Genome DNA | 2 μl (100 ng) |
| Forward Primer mix | 2 μl (20 pmol/tube) |
| Reverse Primer mix | 2 μl (20 pmol/tube) |
| Cy-3dUTP (1 mM) | 2 μl (2 pmol/tube) |
| $H_2O$ | 17 μl |
| Total | 50 μl |

The reaction fluid of the above composition was subjected to amplification reaction with a commercially-available thermal cycler, according to the following protocol.

| | | |
|---|---|---|
| 95° C. | 10 min. | |
| 92° C. | 45 sec. | ←↑ |
| 55° C. | 45 sec. | 35 cycles |
| 72° C. | 45 sec. | →↑ |
| 72° C. | 10 min. | |

Following reaction, the primer was removed using a purification column (QIAGEN QIAquick PCR Purification Kit), after which the amplified product was quantified, and taken as a labeled specimen.

<6. Hybridization>

The DNA microarray fabricated in "4. Fabricating the DNA microarray" and the labeled specimen fabricated in "5. Amplification and labeling of specimen (PCR amplification and fluorescent label inclusion)" were used for the detection reaction.

(6-1. Blocking of the DNA Microarray)

BSA (bovine serum albumin Fraction V, manufactured by Sigma Chemical Co.) was dissolved in 100 mM NaCl/10 mM phosphate buffer to 1 percent by weight, the DNA microarray fabricated in "4. Fabricating the DNA microarray" was immersed in this solution for 2 hours at room temperature, thereby performing blocking. Following the blocking, the article was washed with a 2×SSC solution (300 mM of NaCl and 30 mM of sodium citrate (trisodium citrate dihydrate, $C_6H_5Na_3 \cdot 2H_2O$), pH 7.0) containing 0.1 percent by weight of SDS (sodium dodecyl sulfate), rinsed with pure water, and the spin dried with a spin drying device.

(6-2. Hybridization)

The spin-dried DNA microarray was set in a hybridization device (Hybridization Station manufactured by Genomic Solutions Inc.), and a hybridization reaction was carried out with the hybridization solution and under the conditions shown below.

Hybridization Solution
   6×SSPE/10% formamide/Target (all 2nd PCR products)
   (6×SSPE: 900 mM of NaCl, 60 mM of $NaH_2PO_4 \times H_2O$, 6 mM of EDTA, pH 7.4)

Hybridization Conditions
   65° C. 3 minutes→92° C. 2 minutes→45° C. 3 hours→Wash 2×SSC/0.1% SDS at 25° C.→Wash 2×SSC at 20° C.→(manually wash with $H_2O$)→spin dry That is to say, the hybridization reaction was carried out for 3 minutes at 65° C., 2 minutes at 92° C., and 3 hours at 45° C., and then cleansed with 2×SSC/0.1% SDS at 25° C. and 2×SSC at 20° C., and finally rinsed with purified water and spin-dried.

<7. Detecting Microorganism (Fluorescence Measurement)>

The DNA microarray following the hybridization reaction was subjected to fluorescence measurement using a DNA microarray fluorescence detecting device (GenePix 4000B, manufactured by Axon Instruments, Inc.). Excellent discrimination results were obtained with each of the probes.

Other Embodiments

Note that it is needless to say that the objects of the present invention can be achieved by supplying to a system or device a storage medium storing program code for software for realizing the functions of the above-described embodiment, and a computer (or CPU or MPU) of the system or device reading out and executing the program code stored in the storage medium. In this case, the program code itself read out from the storage medium realizes the functions of the above-described embodiment, and the storage medium storing the program code makes up the present invention.

Examples of storage media for supplying program code include diskettes, hard disks, optical disks, magneto-optical disks, CD-ROMS, CD-Rs, magnetic tape, non-volatile memory cards, ROM, and so forth.

It is also needless to say that the present invention is not restricted to cases wherein the functions of the above-described embodiment are realized by a computer executing the program code read out; rather, the present invention also includes cases wherein an operating system or the like operating on the computer performs part or all of the actual processing based on instructions of the program code, thereby realizing the functions of the above-described embodiment.

Further, it is needless to say that the present invention also includes cases wherein the program code read out from the storage medium is written to memory provided to a function expansion board inserted into the computer or to a function expansion unit connected to the computer, following which a CPU or the like provided to the function expansion board or the function expansion unit performs part or all of the actual processing based on instructions of the program code, thereby realizing the functions of the above-described embodiment.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An information processing method for designing a DNA probe, said method comprising:
   a first counting step for counting, with regard to a first base sequence data group containing a target base sequence, the number of times of manifestation of each of a plurality of partial base sequences obtained from data of said target base sequence, and holding frequency information obtained by said counting;
   a second counting step for counting, with regard to a second base sequence data group to be distinguished from said first base sequence data group, the number of times of manifestation of each of said plurality of partial base sequences, and holding frequency information obtained by said counting;
   an identification step for identifying probe candidates based on frequency information held in said first and second counting steps; and
   an outputting step for outputting the probe candidates to an input/output device or a user.

2. An information processing method for designing a DNA probe according to claim 1, wherein said identification step for identifying probe candidates based on frequency information held in said first and second counting steps comprises:
   a display step for displaying frequency information held in said first and second counting steps, so as to be comparable with reference to said plurality of partial base sequences; and
   a determining step for determining at least one of said plurality of partial base sequences according to instruction operations made by a user, and identifying probe candidates based on the determined partial base sequences.

3. An information processing method for designing a DNA probe according to claim 2, further comprising in addition to said first and second counting steps, a third counting step for counting, with regard to said first base sequence data group and said second base sequence data group, the position and length of partial base sequences common to both, and holding information obtained thereby.

4. An information processing method for designing a DNA probe according to claim 3, wherein probe creating is performed with regard to regions between common base sequences obtained in said third counting step.

5. An information processing method for designing a DNA probe according to claim 3, wherein probe creating is performed with regard to all regions between common base sequences obtained in said third counting step.

6. An information processing method for designing a DNA probe according to claim 1, wherein said first base sequence data group is base sequence data including a plurality of polymorphs of a target organism species, and wherein said second base sequence data group is base sequence data including a plurality of polymorphs of a organism species other than said target organism species.

7. An information processing method for designing a DNA probe according to claim 1, further comprising a first selecting step for selecting probe candidates to be used for a probe set with regard to probe candidates formed in said identification step, by adding and deleting bases at the head and end such that the melting temperature is around the same as that of other probes making up the probe set.

8. An information processing method for designing a DNA probe according to claim 1, further comprising a first selecting step for calculating the probe melting temperature for the probe candidates formed in said identification step, and selecting probe candidates to be used for a probe set based on the calculated melting temperature.

9. An information processing method for designing a DNA probe according to claim 1, further comprising a second selecting step for calculating the probability of formation of secondary structures with regard to the probe candidates formed in said identification step, and selecting probe candidates to be used for a probe set based on the calculation results.

10. An information processing method for designing a DNA probe according to claim 1, further comprising a third selecting step for calculating a degree of matching with regard to the probe candidates formed in said identification step, and selecting probe candidates to be used for a probe set based on the degree of matching.

11. A DNA probe design device comprising:
    first counting means for counting, with regard to a first base sequence data group containing a target base sequence, the number of times of manifestation of each of a plurality of partial base sequences obtained from data of said target base sequence, and holding frequency information obtained by said counting;
    second counting means for counting, with regard to a second base sequence data group to be distinguished from said first base sequence data group, the number of times of manifestation of each of said plurality of partial base sequences, and holding frequency information obtained by said counting;
    display means for displaying frequency information held by said first and second counting means, so as to be comparable with reference to said plurality of partial base sequences;
    identification means for determining at least one of said plurality of partial base sequences according to instruction operations made by a user, and identifying probe candidates based on the determined partial base sequences; and
    an output/output device for outputting the probe candidates to a user.

12. A DNA probe design device according to claim 11, further comprising in addition to said first and second counting means, third counting means for counting, with regard to said first base sequence data group and said second base sequence data group, the position and length of partial base sequences common to both, and holding information obtained thereby.

13. A DNA probe design device according to claim 12, wherein said display means add common information held by said third counting means to the frequency information held by said first and second counting means, and display the information so as to be comparable with reference to said plurality of partial base sequences.

14. A DNA probe design device according to claim 12, wherein probe creating is performed with regard to regions between common base sequences obtained in said third counting means.

15. A control program stored on a computer readable medium for causing a computer to execute the information processing method for designing a DNA probe according to claim 1.

16. A storage medium storing a control program for causing a computer to execute the information processing method for designing a DNA probe according to claim 1.

* * * * *

UNITED STATES PATENT AND TRADEMARK OFFICE
CERTIFICATE OF CORRECTION

| | |
|---|---|
| PATENT NO. | : 7,283,912 B2 |
| APPLICATION NO. | : 10/805292 |
| DATED | : October 16, 2007 |
| INVENTOR(S) | : Hiroto Yoshii et al. |

It is certified that error appears in the above-identified patent and that said Letters Patent is hereby corrected as shown below:

COLUMN 2:

Line 20, "steps-may" should read --steps may--.

COLUMN 4:

Line 41, "invention" should read --invention.--.

COLUMN 5:

Line 46, "may" should read --many--.

COLUMN 8:

Line 26, "base" (first occurrence) should be deleted.

COLUMN 9:

Line 24, "can" should read --can be--.

COLUMN 15:

Line 65, "sequences." should read --sequences).--.

COLUMN 16:

Line 23, "may be also be" should read --may also be--.

COLUMN 17:

Line 17, "hat" should read --that--; and
Line 36, "the from" should be deleted.

UNITED STATES PATENT AND TRADEMARK OFFICE
CERTIFICATE OF CORRECTION

PATENT NO. : 7,283,912 B2
APPLICATION NO. : 10/805292
DATED : October 16, 2007
INVENTOR(S) : Hiroto Yoshii et al.

It is certified that error appears in the above-identified patent and that said Letters Patent is hereby corrected as shown below:

<u>COLUMN 19</u>:

Line 55, "method," should read --the method. --.

<u>COLUMN 22</u>:

Line 34, "form" should read --from--.

<u>COLUMN 77</u>:

Line 55, "a" should read --an--.

<u>COLUMN 78</u>:

Line 49, "add" should read --adds--; and
Line 51, "display" should read --displays--.

Signed and Sealed this

Third Day of June, 2008

JON W. DUDAS
*Director of the United States Patent and Trademark Office*

SEQUENCE LISTING

<160> NUMBER OF SEQ ID NOS: 170

<210> SEQ ID NO 1
<211> LENGTH: 26
<212> TYPE: DNA
<213> ORGANISM: Artificial
<220> FEATURE:
<223> OTHER INFORMATION: Synthesized DNA probe

<400> SEQUENCE: 1
gaaccgcatg gttcaaaagt gaaaga                                          26

<210> SEQ ID NO 2
<211> LENGTH: 24
<212> TYPE: DNA
<213> ORGANISM: Artificial
<220> FEATURE:
<223> OTHER INFORMATION: Synthesized DNA probe

<400> SEQUENCE: 2
cacttataga tggatccgcg ctgc                                            24

<210> SEQ ID NO 3
<211> LENGTH: 26
<212> TYPE: DNA
<213> ORGANISM: Artificial
<220> FEATURE:
<223> OTHER INFORMATION: Synthesized DNA probe

<400> SEQUENCE: 3
tgcacatctt gacggtacct aatcag                                          26

<210> SEQ ID NO 4
<211> LENGTH: 22
<212> TYPE: DNA
<213> ORGANISM: Artificial
<220> FEATURE:
<223> OTHER INFORMATION: Synthesized DNA probe

<400> SEQUENCE: 4 cccctttagtg ctgcagctaa cg                                             22

<210> SEQ ID NO 5
<211> LENGTH: 23
<212> TYPE: DNA
<213> ORGANISM: Artificial
<220> FEATURE:
<223> OTHER INFORMATION: Synthesized DNA probe

<400> SEQUENCE: 5
aatacaaagg gcagcgaaac cgc                                             23

<210> SEQ ID NO 6
<211> LENGTH: 25
<212> TYPE: DNA
<213> ORGANISM: Artificial
<220> FEATURE:
<223> OTHER INFORMATION: Synthesized DNA probe

<400> SEQUENCE: 6
ccggtggagt aaccttttag gagct                                           25

<210> SEQ ID NO 7
<211> LENGTH: 25

```
<212> TYPE: DNA
<213> ORGANISM: Artificial
<220> FEATURE:
<223> OTHER INFORMATION: Synthesized DNA probe

<400> SEQUENCE: 7
taacctttta ggagctagcc gtcga                                          25

<210> SEQ ID NO 8
<211> LENGTH: 23
<212> TYPE: DNA
<213> ORGANISM: Artificial
<220> FEATURE:
<223> OTHER INFORMATION: Synthesized DNA probe

<400> SEQUENCE: 8
tttaggagct agccgtcgaa ggt                                            23

<210> SEQ ID NO 9
<211> LENGTH: 23
<212> TYPE: DNA
<213> ORGANISM: Artificial
<220> FEATURE:
<223> OTHER INFORMATION: Synthesized DNA probe

<400> SEQUENCE: 9
tagccgtcga aggtgggaca aat                                            23

<210> SEQ ID NO 10
<211> LENGTH: 22
<212> TYPE: DNA
<213> ORGANISM: Artificial
<220> FEATURE:
<223> OTHER INFORMATION: Synthesized DNA probe

<400> SEQUENCE: 10
gaacagacga ggagcttgct cc                                             22

<210> SEQ ID NO 11
<211> LENGTH: 26
<212> TYPE: DNA
<213> ORGANISM: Artificial
<220> FEATURE:
<223> OTHER INFORMATION: Synthesized DNA probe

<400> SEQUENCE: 11
tagtgaaaga cggttttgct gtcact                                         26

<210> SEQ ID NO 12
<211> LENGTH: 26
<212> TYPE: DNA
<213> ORGANISM: Artificial
<220> FEATURE:
<223> OTHER INFORMATION: Synthesized DNA probe

<400> SEQUENCE: 12
taagtaacta tgcacgtctt gacggt                                         26

<210> SEQ ID NO 13
<211> LENGTH: 26
<212> TYPE: DNA
<213> ORGANISM: Artificial
<220> FEATURE:
<223> OTHER INFORMATION: Synthesized DNA probe

<400> SEQUENCE: 13
``` gaccccctcta gagatagagt tttccc                                          26

<210> SEQ ID NO 14
<211> LENGTH: 24
<212> TYPE: DNA
<213> ORGANISM: Artificial
<220> FEATURE:
<223> OTHER INFORMATION: Synthesized DNA probe

<400> SEQUENCE: 14
agtaaccatt tggagctagc cgtc                                              24

<210> SEQ ID NO 15
<211> LENGTH: 23
<212> TYPE: DNA
<213> ORGANISM: Artificial
<220> FEATURE:
<223> OTHER INFORMATION: Synthesized DNA probe

<400> SEQUENCE: 15
gagcttgctc ctctgacgtt agc                                               23

<210> SEQ ID NO 16
<211> LENGTH: 22
<212> TYPE: DNA
<213> ORGANISM: Artificial
<220> FEATURE:
<223> OTHER INFORMATION: Synthesized DNA probe

<400> SEQUENCE: 16
agccggtgga gtaaccattt gg                                                22

<210> SEQ ID NO 17
<211> LENGTH: 22
<212> TYPE: DNA
<213> ORGANISM: Artificial
<220> FEATURE:
<223> OTHER INFORMATION: Synthesized DNA probe

<400> SEQUENCE: 17
ctcttgccat cggatgtgcc ca                                                22

<210> SEQ ID NO 18
<211> LENGTH: 26
<212> TYPE: DNA
<213> ORGANISM: Artificial
<220> FEATURE:
<223> OTHER INFORMATION: Synthesized DNA probe

<400> SEQUENCE: 18
ataccttrgc tcattgacgt tacccg                                            26

<210> SEQ ID NO 19
<211> LENGTH: 24
<212> TYPE: DNA
<213> ORGANISM: Artificial
<220> FEATURE:
<223> OTHER INFORMATION: Synthesized DNA probe

<400> SEQUENCE: 19
tttgctcatt gacgttaccc gcag                                              24

<210> SEQ ID NO 20
<211> LENGTH: 24
<212> TYPE: DNA
<213> ORGANISM: Artificial

```
<220> FEATURE:
<223> OTHER INFORMATION: Synthesized DNA probe

<400> SEQUENCE: 20
actggcaagc ttgagtctcg taga                                              24

<210> SEQ ID NO 21
<211> LENGTH: 23
<212> TYPE: DNA
<213> ORGANISM: Artificial
<220> FEATURE:
<223> OTHER INFORMATION: Synthesized DNA probe

<400> SEQUENCE: 21
atacaaagag aagcgacctc gcg                                               23

<210> SEQ ID NO 22
<211> LENGTH: 25
<212> TYPE: DNA
<213> ORGANISM: Artificial
<220> FEATURE:
<223> OTHER INFORMATION: Synthesized DNA probe

<400> SEQUENCE: 22
cggacctcat aaagtgcgtc gtagt                                             25

<210> SEQ ID NO 23
<211> LENGTH: 26
<212> TYPE: DNA
<213> ORGANISM: Artificial
<220> FEATURE:
<223> OTHER INFORMATION: Synthesized DNA probe

<400> SEQUENCE: 23
gcggggagga agggagtaaa gttaat                                            26

<210> SEQ ID NO 24
<211> LENGTH: 23
<212> TYPE: DNA
<213> ORGANISM: Artificial
<220> FEATURE:
<223> OTHER INFORMATION: Synthesized DNA probe

<400> SEQUENCE: 24
tagcacagag agcttgctct cgg                                               23

<210> SEQ ID NO 25
<211> LENGTH: 23
<212> TYPE: DNA
<213> ORGANISM: Artificial
<220> FEATURE:
<223> OTHER INFORMATION: Synthesized DNA probe

<400> SEQUENCE: 25
tcatgccatc agatgtgccc aga                                               23

<210> SEQ ID NO 26
<211> LENGTH: 25
<212> TYPE: DNA
<213> ORGANISM: Artificial
<220> FEATURE:
<223> OTHER INFORMATION: Synthesized DNA probe

<400> SEQUENCE: 26
cggggaggaa ggcgataagg ttaat                                             25
```

<210> SEQ ID NO 27
<211> LENGTH: 25
<212> TYPE: DNA
<213> ORGANISM: Artificial
<220> FEATURE:
<223> OTHER INFORMATION: Synthesized DNA probe

<400> SEQUENCE: 27
ttcgattgac gttacccgca gaaga                                   25

<210> SEQ ID NO 28
<211> LENGTH: 26
<212> TYPE: DNA
<213> ORGANISM: Artificial
<220> FEATURE:
<223> OTHER INFORMATION: Synthesized DNA probe

<400> SEQUENCE: 28
ggtctgtcaa gtcggatgtg aaatcc                                  26

<210> SEQ ID NO 29
<211> LENGTH: 24
<212> TYPE: DNA
<213> ORGANISM: Artificial
<220> FEATURE:
<223> OTHER INFORMATION: Synthesized DNA probe

<400> SEQUENCE: 29
gcaggctaga gtcttgtaga gggg                                    24

<210> SEQ ID NO 30
<211> LENGTH: 24
<212> TYPE: DNA
<213> ORGANISM: Artificial
<220> FEATURE:
<223> OTHER INFORMATION: Synthesized DNA probe

<400> SEQUENCE: 30
tgagggagaa agtgggggat cttc                                    24

<210> SEQ ID NO 31
<211> LENGTH: 25
<212> TYPE: DNA
<213> ORGANISM: Artificial
<220> FEATURE:
<223> OTHER INFORMATION: Synthesized DNA probe

<400> SEQUENCE: 31
tcagatgagc ctaggtcgga ttagc                                   25

<210> SEQ ID NO 32
<211> LENGTH: 24
<212> TYPE: DNA
<213> ORGANISM: Artificial
<220> FEATURE:
<223> OTHER INFORMATION: Synthesized DNA probe

<400> SEQUENCE: 32
gagctagagt acggtagagg gtgg                                    24

<210> SEQ ID NO 33
<211> LENGTH: 25
<212> TYPE: DNA
<213> ORGANISM: Artificial
<220> FEATURE:
<223> OTHER INFORMATION: Synthesized DNA probe

```
<400> SEQUENCE: 33
gtacggtaga gggtggtgga atttc                                              25

<210> SEQ ID NO 34
<211> LENGTH: 24
<212> TYPE: DNA
<213> ORGANISM: Artificial
<220> FEATURE:
<223> OTHER INFORMATION: Synthesized DNA probe

<400> SEQUENCE: 34
gaccacctgg actgatactg acac                                               24

<210> SEQ ID NO 35
<211> LENGTH: 25
<212> TYPE: DNA
<213> ORGANISM: Artificial
<220> FEATURE:
<223> OTHER INFORMATION: Synthesized DNA probe

<400> SEQUENCE: 35
tggccttgac atgctgagaa ctttc                                              25

<210> SEQ ID NO 36
<211> LENGTH: 23
<212> TYPE: DNA
<213> ORGANISM: Artificial
<220> FEATURE:
<223> OTHER INFORMATION: Synthesized DNA probe

<400> SEQUENCE: 36
ttagttacca gcacctcggg tgg                                                23

<210> SEQ ID NO 37
<211> LENGTH: 22
<212> TYPE: DNA
<213> ORGANISM: Artificial
<220> FEATURE:
<223> OTHER INFORMATION: Synthesized DNA probe

<400> SEQUENCE: 37
tagtctaacc gcaaggggga cg                                                 22

<210> SEQ ID NO 38
<211> LENGTH: 23
<212> TYPE: DNA
<213> ORGANISM: Artificial
<220> FEATURE:
<223> OTHER INFORMATION: Synthesized DNA probe

<400> SEQUENCE: 38
tagcacaggg gagcttgctc cct                                                23

<210> SEQ ID NO 39
<211> LENGTH: 25
<212> TYPE: DNA
<213> ORGANISM: Artificial
<220> FEATURE:
<223> OTHER INFORMATION: Synthesized DNA probe

<400> SEQUENCE: 39
aggtggtgaa cttaatacgc tcatc                                              25

<210> SEQ ID NO 40
```

```
<211> LENGTH: 26
<212> TYPE: DNA
<213> ORGANISM: Artificial
<220> FEATURE:
<223> OTHER INFORMATION: Synthesized DNA probe

<400> SEQUENCE: 40
tcatcaattg acgttactcg cagaag                                          26

<210> SEQ ID NO 41
<211> LENGTH: 26
<212> TYPE: DNA
<213> ORGANISM: Artificial
<220> FEATURE:
<223> OTHER INFORMATION: Synthesized DNA probe

<400> SEQUENCE: 41
actgcatttg aaactggcaa gctaga                                          26

<210> SEQ ID NO 42
<211> LENGTH: 22
<212> TYPE: DNA
<213> ORGANISM: Artificial
<220> FEATURE:
<223> OTHER INFORMATION: Synthesized DNA probe

<400> SEQUENCE: 42
ttatcctttg ttgccagcgg tt                                              22

<210> SEQ ID NO 43
<211> LENGTH: 23
<212> TYPE: DNA
<213> ORGANISM: Artificial
<220> FEATURE:
<223> OTHER INFORMATION: Synthesized DNA probe

<400> SEQUENCE: 43
actttcagcg aggaggaagg tgg                                             23

<210> SEQ ID NO 44
<211> LENGTH: 25
<212> TYPE: DNA
<213> ORGANISM: Artificial
<220> FEATURE:
<223> OTHER INFORMATION: Synthesized DNA probe

<400> SEQUENCE: 44
agtagaacgc tgaaggagga gcttg                                           25

<210> SEQ ID NO 45
<211> LENGTH: 25
<212> TYPE: DNA
<213> ORGANISM: Artificial
<220> FEATURE:
<223> OTHER INFORMATION: Synthesized DNA probe

<400> SEQUENCE: 45
cttgcatcac taccagatgg acctg                                           25

<210> SEQ ID NO 46
<211> LENGTH: 26
<212> TYPE: DNA
<213> ORGANISM: Artificial
<220> FEATURE:
<223> OTHER INFORMATION: Synthesized DNA probe

<400> SEQUENCE: 46
```

```
tgagagtgga aagttcacac tgtgac                                26

<210> SEQ ID NO 47
<211> LENGTH: 26
<212> TYPE: DNA
<213> ORGANISM: Artificial
<220> FEATURE:
<223> OTHER INFORMATION: Synthesized DNA probe

<400> SEQUENCE: 47
gctgtggctt aaccatagta ggcttt                                26

<210> SEQ ID NO 48
<211> LENGTH: 23
<212> TYPE: DNA
<213> ORGANISM: Artificial
<220> FEATURE:
<223> OTHER INFORMATION: Synthesized DNA probe

<400> SEQUENCE: 48
aagcggctct ctggcttgta act                                   23

<210> SEQ ID NO 49
<211> LENGTH: 24
<212> TYPE: DNA
<213> ORGANISM: Artificial
<220> FEATURE:
<223> OTHER INFORMATION: Synthesized DNA probe

<400> SEQUENCE: 49
tagacccttt ccggggttta gtgc                                  24

<210> SEQ ID NO 50
<211> LENGTH: 26
<212> TYPE: DNA
<213> ORGANISM: Artificial
<220> FEATURE:
<223> OTHER INFORMATION: Synthesized DNA probe

<400> SEQUENCE: 50
gacggcaagc taatctctta aagcca                                26

<210> SEQ ID NO 51
<211> LENGTH: 24
<212> TYPE: DNA
<213> ORGANISM: Artificial
<220> FEATURE:
<223> OTHER INFORMATION: Synthesized DNA probe

<400> SEQUENCE: 51
gcttgggaat ctggcttatg gagg                                  24

<210> SEQ ID NO 52
<211> LENGTH: 23
<212> TYPE: DNA
<213> ORGANISM: Artificial
<220> FEATURE:
<223> OTHER INFORMATION: Synthesized DNA probe

<400> SEQUENCE: 52
tgccatagga tgagcccaag tgg                                   23

<210> SEQ ID NO 53
<211> LENGTH: 26
<212> TYPE: DNA
```

<213> ORGANISM: Artificial
<220> FEATURE:
<223> OTHER INFORMATION: Synthesized DNA probe

<400> SEQUENCE: 53
cttgggaatg tactgacgct catgtg                        26

<210> SEQ ID NO 54
<211> LENGTH: 23
<212> TYPE: DNA
<213> ORGANISM: Artificial
<220> FEATURE:
<223> OTHER INFORMATION: Synthesized DNA probe

<400> SEQUENCE: 54
ggattgggct tagagcttgg tgc                           23

<210> SEQ ID NO 55
<211> LENGTH: 22
<212> TYPE: DNA
<213> ORGANISM: Artificial
<220> FEATURE:
<223> OTHER INFORMATION: Synthesized DNA probe

<400> SEQUENCE: 55
tacagaggga agcgaagctg cg                            22

<210> SEQ ID NO 56
<211> LENGTH: 26
<212> TYPE: DNA
<213> ORGANISM: Artificial
<220> FEATURE:
<223> OTHER INFORMATION: Synthesized DNA probe

<400> SEQUENCE: 56
ggcgtttacc acggtatgat tcatga                        26

<210> SEQ ID NO 57
<211> LENGTH: 23
<212> TYPE: DNA
<213> ORGANISM: Artificial
<220> FEATURE:
<223> OTHER INFORMATION: Synthesized DNA probe

<400> SEQUENCE: 57
aatgcctacc aagcctgcga tct                           23

<210> SEQ ID NO 58
<211> LENGTH: 25
<212> TYPE: DNA
<213> ORGANISM: Artificial
<220> FEATURE:
<223> OTHER INFORMATION: Synthesized DNA probe

<400> SEQUENCE: 58
tatcggaaga tgaaagtgcg ggact                         25

<210> SEQ ID NO 59
<211> LENGTH: 22
<212> TYPE: DNA
<213> ORGANISM: Artificial
<220> FEATURE:
<223> OTHER INFORMATION: Synthesized DNA probe

<400> SEQUENCE: 59
cagagagctt gctctcgggt ga                            22

<210> SEQ ID NO 60
<211> LENGTH: 26
<212> TYPE: DNA
<213> ORGANISM: Artificial
<220> FEATURE:
<223> OTHER INFORMATION: Synthesized DNA probe

<400> SEQUENCE: 60
gggaggaagg tgttgtggtt aataac                                26

<210> SEQ ID NO 61
<211> LENGTH: 26
<212> TYPE: DNA
<213> ORGANISM: Artificial
<220> FEATURE:
<223> OTHER INFORMATION: Synthesized DNA probe

<400> SEQUENCE: 61
ggtgttgtgg ttaataacca cagcaa                                26

<210> SEQ ID NO 62
<211> LENGTH: 22
<212> TYPE: DNA
<213> ORGANISM: Artificial
<220> FEATURE:
<223> OTHER INFORMATION: Synthesized DNA probe

<400> SEQUENCE: 62
gcggtctgtc aagtcggatg tg                                    22

<210> SEQ ID NO 63
<211> LENGTH: 25
<212> TYPE: DNA
<213> ORGANISM: Artificial
<220> FEATURE:
<223> OTHER INFORMATION: Synthesized DNA probe

<400> SEQUENCE: 63
attcgaaact ggcaggctag agtct                                 25

<210> SEQ ID NO 64
<211> LENGTH: 25
<212> TYPE: DNA
<213> ORGANISM: Artificial
<220> FEATURE:
<223> OTHER INFORMATION: Synthesized DNA probe

<400> SEQUENCE: 64
taaccacagc aattgacgtt acccg                                 25

<210> SEQ ID NO 65
<211> LENGTH: 24
<212> TYPE: DNA
<213> ORGANISM: Artificial
<220> FEATURE:
<223> OTHER INFORMATION: Synthesized DNA probe

<400> SEQUENCE: 65
gcaattgacg ttacccgcag aaga                                  24

<210> SEQ ID NO 66
<211> LENGTH: 23
<212> TYPE: DNA
<213> ORGANISM: Artificial
<220> FEATURE:

<223> OTHER INFORMATION: Synthesized DNA probe

<400> SEQUENCE: 66
ttctttcctc ccgagtgctt gca                                        23

<210> SEQ ID NO 67
<211> LENGTH: 25
<212> TYPE: DNA
<213> ORGANISM: Artificial
<220> FEATURE:
<223> OTHER INFORMATION: Synthesized DNA probe

<400> SEQUENCE: 67
aacacgtggg taacctaccc atcag                                      25

<210> SEQ ID NO 68
<211> LENGTH: 24
<212> TYPE: DNA
<213> ORGANISM: Artificial
<220> FEATURE:
<223> OTHER INFORMATION: Synthesized DNA probe

<400> SEQUENCE: 68
atggcataag agtgaaaggc gctt                                       24

<210> SEQ ID NO 69
<211> LENGTH: 22
<212> TYPE: DNA
<213> ORGANISM: Artificial
<220> FEATURE:
<223> OTHER INFORMATION: Synthesized DNA probe

<400> SEQUENCE: 69
gacccgcggt gcattagcta gt                                         22

<210> SEQ ID NO 70
<211> LENGTH: 25
<212> TYPE: DNA
<213> ORGANISM: Artificial
<220> FEATURE:
<223> OTHER INFORMATION: Synthesized DNA probe

<400> SEQUENCE: 70
ggacgttagt aactgaacgt cccct                                      25

<210> SEQ ID NO 71
<211> LENGTH: 22
<212> TYPE: DNA
<213> ORGANISM: Artificial
<220> FEATURE:
<223> OTHER INFORMATION: Synthesized DNA probe

<400> SEQUENCE: 71
ctcaaccggg gagggtcatt gg                                         22

<210> SEQ ID NO 72
<211> LENGTH: 22
<212> TYPE: DNA
<213> ORGANISM: Artificial
<220> FEATURE:
<223> OTHER INFORMATION: Synthesized DNA probe

<400> SEQUENCE: 72
ttggagggtt tccgcccttc ag                                         22

```
<210> SEQ ID NO 73
<211> LENGTH: 23
<212> TYPE: DNA
<213> ORGANISM: Artificial
<220> FEATURE:
<223> OTHER INFORMATION: Synthesized DNA for forward primer named F1

<400> SEQUENCE: 73
gcggcgtgcc taatacatgc aag                                               23

<210> SEQ ID NO 74
<211> LENGTH: 23
<212> TYPE: DNA
<213> ORGANISM: Artificial
<220> FEATURE:
<223> OTHER INFORMATION: Synthesized DNA for forward primer named F2

<400> SEQUENCE: 74
gcggcaggcc taacacatgc aag                                               23

<210> SEQ ID NO 75
<211> LENGTH: 23
<212> TYPE: DNA
<213> ORGANISM: Artificial
<220> FEATURE:
<223> OTHER INFORMATION: Synthesized DNA for forward primer named F3

<400> SEQUENCE: 75
gcggcaggct taacacatgc aag                                               23

<210> SEQ ID NO 76
<211> LENGTH: 22
<212> TYPE: DNA
<213> ORGANISM: Artificial
<220> FEATURE:
<223> OTHER INFORMATION: Synthesized DNA for reverse primer named R1

<400> SEQUENCE: 76
atccagccgc accttccgat ac                                                22

<210> SEQ ID NO 77
<211> LENGTH: 22
<212> TYPE: DNA
<213> ORGANISM: Artificial
<220> FEATURE:
<223> OTHER INFORMATION: Synthesized DNA for reverse primer named R2

<400> SEQUENCE: 77
atccaaccgc aggttcccct ac                                                22

<210> SEQ ID NO 78
<211> LENGTH: 22
<212> TYPE: DNA
<213> ORGANISM: Artificial
<220> FEATURE:
<223> OTHER INFORMATION: Synthesized DNA for reverse primer named R3

<400> SEQUENCE: 78
atccagccgc aggttcccct ac                                                22

<210> SEQ ID NO 79
<211> LENGTH: 26
<212> TYPE: DNA
<213> ORGANISM: Artificial
<220> FEATURE:
<223> OTHER INFORMATION: Synthesized DNA probe
```

-continued

<400> SEQUENCE: 79
tctttcactt ttgaaccatg cggttc                                      26

<210> SEQ ID NO 80
<211> LENGTH: 24
<212> TYPE: DNA
<213> ORGANISM: Artificial
<220> FEATURE:
<223> OTHER INFORMATION: Synthesized DNA probe

<400> SEQUENCE: 80
gcagcgcgga tccatctata agtg                                        24

<210> SEQ ID NO 81
<211> LENGTH: 26
<212> TYPE: DNA
<213> ORGANISM: Artificial
<220> FEATURE:
<223> OTHER INFORMATION: Synthesized DNA probe

<400> SEQUENCE: 81
ctgattaggt accgtcaaga tgtgca                                      26

<210> SEQ ID NO 82
<211> LENGTH: 22
<212> TYPE: DNA
<213> ORGANISM: Artificial
<220> FEATURE:
<223> OTHER INFORMATION: Synthesized DNA probe

<400> SEQUENCE: 82
cgttagctgc agcactaagg gg                                          22

<210> SEQ ID NO 83
<211> LENGTH: 23
<212> TYPE: DNA
<213> ORGANISM: Artificial
<220> FEATURE:
<223> OTHER INFORMATION: Synthesized DNA probe

<400> SEQUENCE: 83
gcggtttcgc tgccctttgt att                                         23

<210> SEQ ID NO 84
<211> LENGTH: 25
<212> TYPE: DNA
<213> ORGANISM: Artificial
<220> FEATURE:
<223> OTHER INFORMATION: Synthesized DNA probe

<400> SEQUENCE: 84
agctcctaaa aggttactcc accgg                                       25

<210> SEQ ID NO 85
<211> LENGTH: 25
<212> TYPE: DNA
<213> ORGANISM: Artificial
<220> FEATURE:
<223> OTHER INFORMATION: Synthesized DNA probe

<400> SEQUENCE: 85
tcgacggcta gctcctaaaa ggtta                                       25

<210> SEQ ID NO 86
<211> LENGTH: 23

```
<210> SEQ ID NO 86
<211> LENGTH: 23
<212> TYPE: DNA
<213> ORGANISM: Artificial
<220> FEATURE:
<223> OTHER INFORMATION: Synthesized DNA probe

<400> SEQUENCE: 86
accttcgacg gctagctcct aaa                                                23

<210> SEQ ID NO 87
<211> LENGTH: 23
<212> TYPE: DNA
<213> ORGANISM: Artificial
<220> FEATURE:
<223> OTHER INFORMATION: Synthesized DNA probe

<400> SEQUENCE: 87
atttgtccca ccttcgacgg cta                                                23

<210> SEQ ID NO 88
<211> LENGTH: 22
<212> TYPE: DNA
<213> ORGANISM: Artificial
<220> FEATURE:
<223> OTHER INFORMATION: Synthesized DNA probe

<400> SEQUENCE: 88
ggagcaagct cctcgtctgt tc                                                 22

<210> SEQ ID NO 89
<211> LENGTH: 26
<212> TYPE: DNA
<213> ORGANISM: Artificial
<220> FEATURE:
<223> OTHER INFORMATION: Synthesized DNA probe

<400> SEQUENCE: 89
agtgacagca aaaccgtctt tcacta                                             26

<210> SEQ ID NO 90
<211> LENGTH: 26
<212> TYPE: DNA
<213> ORGANISM: Artificial
<220> FEATURE:
<223> OTHER INFORMATION: Synthesized DNA probe

<400> SEQUENCE: 90
accgtcaaga cgtgcatagt tactta                                             26

<210> SEQ ID NO 91
<211> LENGTH: 26
<212> TYPE: DNA
<213> ORGANISM: Artificial
<220> FEATURE:
<223> OTHER INFORMATION: Synthesized DNA probe

<400> SEQUENCE: 91
gggaaaactc tatctctaga ggggtc                                             26

<210> SEQ ID NO 92
<211> LENGTH: 24
<212> TYPE: DNA
<213> ORGANISM: Artificial
<220> FEATURE:
<223> OTHER INFORMATION: Synthesized DNA probe

<400> SEQUENCE: 92
```
gacggctagc tccaaatggt tact                                          24

<210> SEQ ID NO 93
<211> LENGTH: 23
<212> TYPE: DNA
<213> ORGANISM: Artificial
<220> FEATURE:
<223> OTHER INFORMATION: Synthesized DNA probe

<400> SEQUENCE: 93
gctaacgtca gaggagcaag ctc                                           23

<210> SEQ ID NO 94
<211> LENGTH: 22
<212> TYPE: DNA
<213> ORGANISM: Artificial
<220> FEATURE:
<223> OTHER INFORMATION: Synthesized DNA probe

<400> SEQUENCE: 94
ccaaatggtt actccaccgg ct                                            22

<210> SEQ ID NO 95
<211> LENGTH: 22
<212> TYPE: DNA
<213> ORGANISM: Artificial
<220> FEATURE:
<223> OTHER INFORMATION: Synthesized DNA probe

<400> SEQUENCE: 95
tgggcacatc cgatggcaag ag                                            22

<210> SEQ ID NO 96
<211> LENGTH: 26
<212> TYPE: DNA
<213> ORGANISM: Artificial
<220> FEATURE:
<223> OTHER INFORMATION: Synthesized DNA probe

<400> SEQUENCE: 96
cgggtaacgt caatgagcaa aggtat                                        26

<210> SEQ ID NO 97
<211> LENGTH: 24
<212> TYPE: DNA
<213> ORGANISM: Artificial
<220> FEATURE:
<223> OTHER INFORMATION: Synthesized DNA probe

<400> SEQUENCE: 97
ctgcgggtaa cgtcaatgag caaa                                          24

<210> SEQ ID NO 98
<211> LENGTH: 24
<212> TYPE: DNA
<213> ORGANISM: Artificial
<220> FEATURE:
<223> OTHER INFORMATION: Synthesized DNA probe

<400> SEQUENCE: 98
tctacgagac tcaagcttgc cagt                                          24

<210> SEQ ID NO 99
<211> LENGTH: 23
<212> TYPE: DNA
<213> ORGANISM: Artificial

```
<220> FEATURE:
<223> OTHER INFORMATION: Synthesized DNA probe

<400> SEQUENCE: 99
cgcgaggtcg cttctctttg tat                                           23

<210> SEQ ID NO 100
<211> LENGTH: 25
<212> TYPE: DNA
<213> ORGANISM: Artificial
<220> FEATURE:
<223> OTHER INFORMATION: Synthesized DNA probe

<400> SEQUENCE: 100
actacgacgc actttatgag gtccg                                         25

<210> SEQ ID NO 101
<211> LENGTH: 26
<212> TYPE: DNA
<213> ORGANISM: Artificial
<220> FEATURE:
<223> OTHER INFORMATION: Synthesized DNA probe

<400> SEQUENCE: 101
attaacttta ctcccttcct ccccgc                                        26

<210> SEQ ID NO 102
<211> LENGTH: 23
<212> TYPE: DNA
<213> ORGANISM: Artificial
<220> FEATURE:
<223> OTHER INFORMATION: Synthesized DNA probe

<400> SEQUENCE: 102
ccgagagcaa gctctctgtg cta                                           23

<210> SEQ ID NO 103
<211> LENGTH: 23
<212> TYPE: DNA
<213> ORGANISM: Artificial
<220> FEATURE:
<223> OTHER INFORMATION: Synthesized DNA probe

<400> SEQUENCE: 103
tctgggcaca tctgatggca tga                                           23

<210> SEQ ID NO 104
<211> LENGTH: 25
<212> TYPE: DNA
<213> ORGANISM: Artificial
<220> FEATURE:
<223> OTHER INFORMATION: Synthesized DNA probe

<400> SEQUENCE: 104
attaacctta tcgccttcct ccccg                                         25

<210> SEQ ID NO 105
<211> LENGTH: 25
<212> TYPE: DNA
<213> ORGANISM: Artificial
<220> FEATURE:
<223> OTHER INFORMATION: Synthesized DNA probe

<400> SEQUENCE: 105
tcttctgcgg gtaacgtcaa tcgaa                                         25
```

```
<210> SEQ ID NO 106
<211> LENGTH: 26
<212> TYPE: DNA
<213> ORGANISM: Artificial
<220> FEATURE:
<223> OTHER INFORMATION: Synthesized DNA probe

<400> SEQUENCE: 106
ggatttcaca tccgacttga cagacc                                              26

<210> SEQ ID NO 107
<211> LENGTH: 24
<212> TYPE: DNA
<213> ORGANISM: Artificial
<220> FEATURE:
<223> OTHER INFORMATION: Synthesized DNA probe

<400> SEQUENCE: 107
cccctctaca agactctagc ctgc                                                24

<210> SEQ ID NO 108
<211> LENGTH: 24
<212> TYPE: DNA
<213> ORGANISM: Artificial
<220> FEATURE:
<223> OTHER INFORMATION: Synthesized DNA probe

<400> SEQUENCE: 108
gaagatcccc cactttctcc ctca                                                24

<210> SEQ ID NO 109
<211> LENGTH: 25
<212> TYPE: DNA
<213> ORGANISM: Artificial
<220> FEATURE:
<223> OTHER INFORMATION: Synthesized DNA probe

<400> SEQUENCE: 109
gctaatccga cctaggctca tctga                                               25

<210> SEQ ID NO 110
<211> LENGTH: 24
<212> TYPE: DNA
<213> ORGANISM: Artificial
<220> FEATURE:
<223> OTHER INFORMATION: Synthesized DNA probe

<400> SEQUENCE: 110
ccaccctcta ccgtactcta gctc                                                24

<210> SEQ ID NO 111
<211> LENGTH: 25
<212> TYPE: DNA
<213> ORGANISM: Artificial
<220> FEATURE:
<223> OTHER INFORMATION: Synthesized DNA probe

<400> SEQUENCE: 111
gaaattccac caccctctac cgtac                                               25

<210> SEQ ID NO 112
<211> LENGTH: 24
<212> TYPE: DNA
<213> ORGANISM: Artificial
<220> FEATURE:
<223> OTHER INFORMATION: Synthesized DNA probe
```

```
<400> SEQUENCE: 112
gtgtcagtat cagtccaggt ggtc                                    24

<210> SEQ ID NO 113
<211> LENGTH: 25
<212> TYPE: DNA
<213> ORGANISM: Artificial
<220> FEATURE:
<223> OTHER INFORMATION: Synthesized DNA probe

<400> SEQUENCE: 113
gaaagttctc agcatgtcaa ggcca                                   25

<210> SEQ ID NO 114
<211> LENGTH: 23
<212> TYPE: DNA
<213> ORGANISM: Artificial
<220> FEATURE:
<223> OTHER INFORMATION: Synthesized DNA probe

<400> SEQUENCE: 114
ccacccgagg tgctggtaac taa                                     23

<210> SEQ ID NO 115
<211> LENGTH: 22
<212> TYPE: DNA
<213> ORGANISM: Artificial
<220> FEATURE:
<223> OTHER INFORMATION: Synthesized DNA probe

<400> SEQUENCE: 115
cgtcccccTT gcggttagac ta                                      22

<210> SEQ ID NO 116
<211> LENGTH: 23
<212> TYPE: DNA
<213> ORGANISM: Artificial
<220> FEATURE:
<223> OTHER INFORMATION: Synthesized DNA probe

<400> SEQUENCE: 116
agggagcaag ctcccctgtg cta                                     23

<210> SEQ ID NO 117
<211> LENGTH: 25
<212> TYPE: DNA
<213> ORGANISM: Artificial
<220> FEATURE:
<223> OTHER INFORMATION: Synthesized DNA probe

<400> SEQUENCE: 117
gatgagcgta ttaagttcac cacct                                   25

<210> SEQ ID NO 118
<211> LENGTH: 26
<212> TYPE: DNA
<213> ORGANISM: Artificial
<220> FEATURE:
<223> OTHER INFORMATION: Synthesized DNA probe

<400> SEQUENCE: 118
cttctgcgag taacgtcaat tgatga                                  26

<210> SEQ ID NO 119
```

```
<211> LENGTH: 26
<212> TYPE: DNA
<213> ORGANISM: Artificial
<220> FEATURE:
<223> OTHER INFORMATION: Synthesized DNA probe

<400> SEQUENCE: 119
tctagcttgc cagtttcaaa tgcagt                                        26

<210> SEQ ID NO 120
<211> LENGTH: 22
<212> TYPE: DNA
<213> ORGANISM: Artificial
<220> FEATURE:
<223> OTHER INFORMATION: Synthesized DNA probe

<400> SEQUENCE: 120
aaccgctggc aacaaaggat aa                                            22

<210> SEQ ID NO 121
<211> LENGTH: 23
<212> TYPE: DNA
<213> ORGANISM: Artificial
<220> FEATURE:
<223> OTHER INFORMATION: Synthesized DNA probe

<400> SEQUENCE: 121
ccaccttcct cctcgctgaa agt                                           23

<210> SEQ ID NO 122
<211> LENGTH: 25
<212> TYPE: DNA
<213> ORGANISM: Artificial
<220> FEATURE:
<223> OTHER INFORMATION: Synthesized DNA probe

<400> SEQUENCE: 122
caagctcctc cttcagcgtt ctact                                         25

<210> SEQ ID NO 123
<211> LENGTH: 25
<212> TYPE: DNA
<213> ORGANISM: Artificial
<220> FEATURE:
<223> OTHER INFORMATION: Synthesized DNA probe

<400> SEQUENCE: 123
caggtccatc tggtagtgat gcaag                                         25

<210> SEQ ID NO 124
<211> LENGTH: 26
<212> TYPE: DNA
<213> ORGANISM: Artificial
<220> FEATURE:
<223> OTHER INFORMATION: Synthesized DNA probe

<400> SEQUENCE: 124
gtcacagtgt gaactttcca ctctca                                        26

<210> SEQ ID NO 125
<211> LENGTH: 26
<212> TYPE: DNA
<213> ORGANISM: Artificial
<220> FEATURE:
<223> OTHER INFORMATION: Synthesized DNA probe

<400> SEQUENCE: 125
```
aaagcctact atggttaagc cacagc                                          26

<210> SEQ ID NO 126
<211> LENGTH: 23
<212> TYPE: DNA
<213> ORGANISM: Artificial
<220> FEATURE:
<223> OTHER INFORMATION: Synthesized DNA probe

<400> SEQUENCE: 126
agttacaagc cagagagccg ctt                                             23

<210> SEQ ID NO 127
<211> LENGTH: 24
<212> TYPE: DNA
<213> ORGANISM: Artificial
<220> FEATURE:
<223> OTHER INFORMATION: Synthesized DNA probe

<400> SEQUENCE: 127
gcactaaacc ccggaaaggg tcta                                            24

<210> SEQ ID NO 128
<211> LENGTH: 26
<212> TYPE: DNA
<213> ORGANISM: Artificial
<220> FEATURE:
<223> OTHER INFORMATION: Synthesized DNA probe

<400> SEQUENCE: 128
tggctttaag agattagctt gccgtc                                          26

<210> SEQ ID NO 129
<211> LENGTH: 24
<212> TYPE: DNA
<213> ORGANISM: Artificial
<220> FEATURE:
<223> OTHER INFORMATION: Synthesized DNA probe

<400> SEQUENCE: 129
cctccataag ccagattccc aagc                                            24

<210> SEQ ID NO 130
<211> LENGTH: 23
<212> TYPE: DNA
<213> ORGANISM: Artificial
<220> FEATURE:
<223> OTHER INFORMATION: Synthesized DNA probe

<400> SEQUENCE: 130
ccacttgggc tcatcctatg gca                                             23

<210> SEQ ID NO 131
<211> LENGTH: 26
<212> TYPE: DNA
<213> ORGANISM: Artificial
<220> FEATURE:
<223> OTHER INFORMATION: Synthesized DNA probe

<400> SEQUENCE: 131
cacatgagcg tcagtacatt cccaag                                          26

<210> SEQ ID NO 132
<211> LENGTH: 23
<212> TYPE: DNA

```
<213> ORGANISM: Artificial
<220> FEATURE:
<223> OTHER INFORMATION: Synthesized DNA probe

<400> SEQUENCE: 132
gcaccaagct ctaagcccaa tcc                                            23

<210> SEQ ID NO 133
<211> LENGTH: 22
<212> TYPE: DNA
<213> ORGANISM: Artificial
<220> FEATURE:
<223> OTHER INFORMATION: Synthesized DNA probe

<400> SEQUENCE: 133
cgcagcttcg cttccctctg ta                                             22

<210> SEQ ID NO 134
<211> LENGTH: 26
<212> TYPE: DNA
<213> ORGANISM: Artificial
<220> FEATURE:
<223> OTHER INFORMATION: Synthesized DNA probe

<400> SEQUENCE: 134
tcatgaatca taccgtggta aacgcc                                         26

<210> SEQ ID NO 135
<211> LENGTH: 23
<212> TYPE: DNA
<213> ORGANISM: Artificial
<220> FEATURE:
<223> OTHER INFORMATION: Synthesized DNA probe

<400> SEQUENCE: 135
agatcgcagg cttggtaggc att                                            23

<210> SEQ ID NO 136
<211> LENGTH: 25
<212> TYPE: DNA
<213> ORGANISM: Artificial
<220> FEATURE:
<223> OTHER INFORMATION: Synthesized DNA probe

<400> SEQUENCE: 136
agtcccgcac tttcatcttc cgata                                          25

<210> SEQ ID NO 137
<211> LENGTH: 23
<212> TYPE: DNA
<213> ORGANISM: Artificial
<220> FEATURE:
<223> OTHER INFORMATION: Synthesized DNA probe

<400> SEQUENCE: 137
tgcaagcact cgggaggaaa gaa                                            23

<210> SEQ ID NO 138
<211> LENGTH: 25
<212> TYPE: DNA
<213> ORGANISM: Artificial
<220> FEATURE:
<223> OTHER INFORMATION: Synthesized DNA probe

<400> SEQUENCE: 138
ctgatgggta ggttacccac gtgtt                                          25
```

```
<210> SEQ ID NO 139
<211> LENGTH: 24
<212> TYPE: DNA
<213> ORGANISM: Artificial
<220> FEATURE:
<223> OTHER INFORMATION: Synthesized DNA probe

<400> SEQUENCE: 139
aagcgccttt cactcttatg ccat                                          24

<210> SEQ ID NO 140
<211> LENGTH: 22
<212> TYPE: DNA
<213> ORGANISM: Artificial
<220> FEATURE:
<223> OTHER INFORMATION: Synthesized DNA probe

<400> SEQUENCE: 140
actagctaat gcaccgcggg tc                                            22

<210> SEQ ID NO 141
<211> LENGTH: 25
<212> TYPE: DNA
<213> ORGANISM: Artificial
<220> FEATURE:
<223> OTHER INFORMATION: Synthesized DNA probe

<400> SEQUENCE: 141
aggggacgtt cagttactaa cgtcc                                         25

<210> SEQ ID NO 142
<211> LENGTH: 22
<212> TYPE: DNA
<213> ORGANISM: Artificial
<220> FEATURE:
<223> OTHER INFORMATION: Synthesized DNA probe

<400> SEQUENCE: 142
ccaatgaccc tccccggttg ag                                            22

<210> SEQ ID NO 143
<211> LENGTH: 22
<212> TYPE: DNA
<213> ORGANISM: Artificial
<220> FEATURE:
<223> OTHER INFORMATION: Synthesized DNA probe

<400> SEQUENCE: 143
ctgaagggcg gaaaccctcc aa                                            22

<210> SEQ ID NO 144
<211> LENGTH: 22
<212> TYPE: DNA
<213> ORGANISM: Artificial
<220> FEATURE:
<223> OTHER INFORMATION: Synthesized DNA probe

<400> SEQUENCE: 144
tcacccgaga gcaagctctc tg                                            22

<210> SEQ ID NO 145
<211> LENGTH: 26
<212> TYPE: DNA
<213> ORGANISM: Artificial
<220> FEATURE:
```

<223> OTHER INFORMATION: Synthesized DNA probe

<400> SEQUENCE: 145
gttattaacc acaacacctt cctccc                                              26

<210> SEQ ID NO 146
<211> LENGTH: 26
<212> TYPE: DNA
<213> ORGANISM: Artificial
<220> FEATURE:
<223> OTHER INFORMATION: Synthesized DNA probe

<400> SEQUENCE: 146
ttgctgtggt tattaaccac aacacc                                              26

<210> SEQ ID NO 147
<211> LENGTH: 22
<212> TYPE: DNA
<213> ORGANISM: Artificial
<220> FEATURE:
<223> OTHER INFORMATION: Synthesized DNA probe

<400> SEQUENCE: 147
cacatccgac ttgacagacc gc                                                  22

<210> SEQ ID NO 148
<211> LENGTH: 25
<212> TYPE: DNA
<213> ORGANISM: Artificial
<220> FEATURE:
<223> OTHER INFORMATION: Synthesized DNA probe

<400> SEQUENCE: 148
agactctagc ctgccagttt cgaat                                               25

<210> SEQ ID NO 149
<211> LENGTH: 25
<212> TYPE: DNA
<213> ORGANISM: Artificial
<220> FEATURE:
<223> OTHER INFORMATION: Synthesized DNA probe

<400> SEQUENCE: 149
cgggtaacgt caattgctgt ggtta                                               25

<210> SEQ ID NO 150
<211> LENGTH: 24
<212> TYPE: DNA
<213> ORGANISM: Artificial
<220> FEATURE:
<223> OTHER INFORMATION: Synthesized DNA probe

<400> SEQUENCE: 150
tcttctgcgg gtaacgtcaa ttgc                                                24

<210> SEQ ID NO 151
<211> LENGTH: 10
<212> TYPE: DNA
<213> ORGANISM: Artificial
<220> FEATURE:
<223> OTHER INFORMATION: DNA exemplified in the drawing

<400> SEQUENCE: 151
tgatgtgaaa                                                                10

<210> SEQ ID NO 152
<211> LENGTH: 24
<212> TYPE: DNA
<213> ORGANISM: Artificial
<220> FEATURE:
<223> OTHER INFORMATION: DNA exemplified in the drawing

<400> SEQUENCE: 152
gcccacggct caaccgtgga gggt                                              24

<210> SEQ ID NO 153
<211> LENGTH: 10
<212> TYPE: DNA
<213> ORGANISM: Artificial
<220> FEATURE:
<223> OTHER INFORMATION: DNA exemplified in the drawing

<400> SEQUENCE: 153
aaactggaaa                                                              10

<210> SEQ ID NO 154
<211> LENGTH: 26
<212> TYPE: DNA
<213> ORGANISM: Artificial
<220> FEATURE:
<223> OTHER INFORMATION: DNA exemplified in the drawing

<400> SEQUENCE: 154
gaaccgcatg gttcaaaagt gaaaga                                            26

<210> SEQ ID NO 155
<211> LENGTH: 24
<212> TYPE: DNA
<213> ORGANISM: Artificial
<220> FEATURE:
<223> OTHER INFORMATION: DNA exemplified in the drawing

<400> SEQUENCE: 155
cacttataga tggatccgcg ctgc                                              24

<210> SEQ ID NO 156
<211> LENGTH: 26
<212> TYPE: DNA
<213> ORGANISM: Artificial
<220> FEATURE:
<223> OTHER INFORMATION: DNA exemplified in the drawing

<400> SEQUENCE: 156
tgcacatctt gacggtacct aatcag                                            26

<210> SEQ ID NO 157
<211> LENGTH: 22
<212> TYPE: DNA
<213> ORGANISM: Artificial
<220> FEATURE:
<223> OTHER INFORMATION: DNA exemplified in the drawing

<400> SEQUENCE: 157
ccccttagtg ctgcagctaa cg                                                22

<210> SEQ ID NO 158
<211> LENGTH: 23
<212> TYPE: DNA
<213> ORGANISM: Artificial
<220> FEATURE:
<223> OTHER INFORMATION: DNA exemplified in the drawing

```
<400> SEQUENCE: 158
aatacaaagg gcagcgaaac cgc                                    23

<210> SEQ ID NO 159
<211> LENGTH: 25
<212> TYPE: DNA
<213> ORGANISM: Artificial
<220> FEATURE:
<223> OTHER INFORMATION: DNA exemplified in the drawing

<400> SEQUENCE: 159
ccggtggagt aaccttttag gagct                                  25

<210> SEQ ID NO 160
<211> LENGTH: 25
<212> TYPE: DNA
<213> ORGANISM: Artificial
<220> FEATURE:
<223> OTHER INFORMATION: DNA exemplified in the drawing

<400> SEQUENCE: 160 taaccttttag ggagctagcc gtcga                                 25

<210> SEQ ID NO 161
<211> LENGTH: 23
<212> TYPE: DNA
<213> ORGANISM: Artificial
<220> FEATURE:
<223> OTHER INFORMATION: DNA exemplified in the drawing

<400> SEQUENCE: 161
tttaggagct agccgtcgaa ggt                                    23

<210> SEQ ID NO 162
<211> LENGTH: 23
<212> TYPE: DNA
<213> ORGANISM: Artificial
<220> FEATURE:
<223> OTHER INFORMATION: DNA exemplified in the drawing

<400> SEQUENCE: 162
tagccgtcga aggtgggaca aat                                    23

<210> SEQ ID NO 163
<211> LENGTH: 10
<212> TYPE: DNA
<213> ORGANISM: Artificial
<220> FEATURE:
<223> OTHER INFORMATION: DNA exemplified in the drawing

<400> SEQUENCE: 163
agtcgagcga                                                   10

<210> SEQ ID NO 164
<211> LENGTH: 10
<212> TYPE: DNA
<213> ORGANISM: Artificial
<220> FEATURE:
<223> OTHER INFORMATION: DNA exemplified in the drawing

<400> SEQUENCE: 164
gcggcggacg                                                   10

<210> SEQ ID NO 165
<211> LENGTH: 30
```

```
<212> TYPE: DNA
<213> ORGANISM: Artificial
<220> FEATURE:
<223> OTHER INFORMATION: DNA exemplified in the drawing

<400> SEQUENCE: 165
acggacgaga agcttgcttc tctgatgtta                                    30

<210> SEQ ID NO 166
<211> LENGTH: 23
<212> TYPE: DNA
<213> ORGANISM: Artificial
<220> FEATURE:
<223> OTHER INFORMATION: DNA exemplified in the drawing

<400> SEQUENCE: 166
acggacgaga agcttgcttc tct                                           23

<210> SEQ ID NO 167
<211> LENGTH: 25
<212> TYPE: DNA
<213> ORGANISM: Artificial
<220> FEATURE:
<223> OTHER INFORMATION: DNA exemplified in the drawing

<400> SEQUENCE: 167
tgtcacttat agatggatcc gcgct                                         25

<210> SEQ ID NO 168
<211> LENGTH: 26
<212> TYPE: DNA
<213> ORGANISM: Artificial
<220> FEATURE:
<223> OTHER INFORMATION: DNA exemplified in the drawing

<400> SEQUENCE: 168
tgtaagtaac tgtgcacatc ttgacg                                        26

<210> SEQ ID NO 169
<211> LENGTH: 26
<212> TYPE: DNA
<213> ORGANISM: Artificial
<220> FEATURE:
<223> OTHER INFORMATION: DNA exemplified in the drawing

<400> SEQUENCE: 169
acaactctag agatagagcc ttcccc                                        26

<210> SEQ ID NO 170
<211> LENGTH: 26
<212> TYPE: DNA
<213> ORGANISM: Artificial
<220> FEATURE:
<223> OTHER INFORMATION: DNA exemplified in the drawing

<400> SEQUENCE: 170
gtggagtaac cttttaggag ctagcc                                        26
```